United States Patent [19]

Lin et al.

[11] Patent Number: 5,948,918

[45] Date of Patent: *Sep. 7, 1999

[54] BIFLAVANOIDS AND DERIVATIVES THEREOF AS ANTIVIRAL AGENTS

[75] Inventors: Yuh-Meei Lin, Naperville; Michael T. Flavin; Ralph Schure, both of Darien; David E. Zembower, Oak Park; Gen-Xian Zhao, Woodridge, all of Ill.

[73] Assignee: MediChem Research, Inc., Lemont, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 09/059,913

[22] Filed: Apr. 14, 1998

Related U.S. Application Data

[62] Division of application No. 08/668,284, Jun. 21, 1996, Pat. No. 5,773,462
[60] Provisional application No. 60/000,465, Jun. 23, 1995.

[30] Foreign Application Priority Data

Jun. 21, 1996 [WO] WIPO ..................... PCT/US96/10718

[51] Int. Cl.⁶ ................................................. C07D 407/10
[52] U.S. Cl. ............................................................. 549/403
[58] Field of Search ............................................. 549/403

[56] References Cited

U.S. PATENT DOCUMENTS 5,354,866  10/1994  Kempf et al. .

FOREIGN PATENT DOCUMENTS

| 0 427 026 B1 | 5/1991 | European Pat. Off. . |
| 3544457 A1 | 12/1985 | Germany . |
| 87200570 | 8/1987 | Japan . |
| 89207203 | 8/1989 | Japan . |
| 1221314 | 9/1989 | Japan . |
| WO97/00679 | 1/1997 | WIPO . |

OTHER PUBLICATIONS

Wleklik, M,; Zahorska, R.; Luczak, M., Interferon—Inducing Activity of Flavonoids. *Acta Microbiologica Polonica*, 1987, 36:1/2, pp. 151–154.
Mucsi, I.; Prágai, B.M., Inhibition of virus multiplication and alteration of cyclic Amp level in cell cultures by flavanoids. *Experimentia* 1984, 41, pp. 930–931.
Ishitsuka H.; Ohsawa, C.; Ohiwa, T.; Umeda I.; Suhara, Y., Antipicornavirus Flavone Ro 09–0179. *Anitmicrob. Ag. Chemo.* 1982. 22(4), pp. 611–616.
Lin, C.; Kan, W., Medical Plants Used for the Treatment of Hepatitis in Taiwan, 1990, *Amer. J. Clin. Med.*, 1990, 18/12, pp. 35–43.
Kurokawa et al., *Chemical Abstracts*, 1996, vol. 124, No. 21, 124:278137k.
Yukawa et al., *Chemical Abstracts*, 1996, vol. 125, No. 125:265061b.
Ben–Hur et al., *Chemical Abstracts*, 1995, vol. 123, No. 123:208776y.

Lin et al., *Chemical Abstracts*, 1989, vol. 111, No. 111:70319v.
Reischle, Karl Georg, *Chemical Abstracts*, 1995, vol. 122, No. 122:64310w.
Kurokawa et al., *Chemical Abstracts*, 1995, vol. 123, No. 123:334v.
Beretz et al., *Chemical Abstracts*, 1979, vol. 91, No. 91:153417v.
Hayashi et al., *Chemical Abstracts*, 1992, vol. 117, No. 117:225793v.
Mucsi et al. ((1992), "Combined Effects of Flavonoids and Acyclovir Against Herpesviruses in Cell Cultures," *Acta Microbiologica Hungarica*, 39, (2), pp. 137–147.
Kadono et al., *Chemical Abstracts*, 1995, vol. 123, No. 123:208781W.
Yoshinori, et al., (1985) "Antiviral Activity of Natural Occuring Flavonoids in vitro," *Chem. Pharm. Bull.*, No. 9, vol. 33, pp. 3881–3886.
Spedding, et al., (1989), "Inhibition of reverse transcriptases by flavonoids", *Antiviral Research*, 12, pp. 99–110.
Lamar–Zarawska, *Chemical Abstracts*, 1984, vol. 100, No. 100:117812r.
Wleklik, et al., *Chemical Abstracts*, vol. 107, No. 107:126702b.
Wleklik, et al, *Chemical Abstracts*, vol. 111, No. 111:173u.
Kozuka, et al., 1990, *Chemical Abstracts*, vol. 113, No. 113:46254r.
DE 3,544,457, *Chemical Abstracts*, vol. 107, No. 107:211872b.
Tokuda et al., *Chemical Abstracts*, vol. 112, No. 112:16256e.
EP 427,026, *Chemical Abstracts*, vol. 115, No.: 115:189759m.
Fujita et al., *Chemical Abstracts*, vol. 115, No. 115:251633w.
Kurokawa, et al., *Chemical Abstracts*, 1996, vol. 124, No. 21, No. 124:278137k.

(List continued on next page.)

*Primary Examiner*—Johann Richter
*Assistant Examiner*—Taofiq A. Solola
*Attorney, Agent, or Firm*—McDonnell, Boehnen, Hulbert & Berghoff

[57] ABSTRACT

Substantially purified antiviral biflavanoids robustaflavone, hinokiflavone, amentoflavone, agathisflavone, volkensiflavone, morelloflavone, rhusflavanone, succedaneaflavanone, GB-1a, and GB-2a are provided. Antiviral biflavanoid derivatives and salt forms thereof, e.g., robustaflavone tetrasulfate potassium salt, and methods for preparing the same are also disclosed. Pharmaceutical compositions which include the antiviral biflavanoids, derivatives or salts thereof are also provided. Also disclosed is an improved method for obtaining substantially pure robustaflavone from plant material. The biflavanoid compounds, derivatives or salts thereof of the invention may be used in a method for treating and/or preventing viral infections caused by viral agents such as influenza, e.g., influenza A and B; hepatitis, e.g., hepatitis B; human immunodeficiency virus, e.g., HIV-1; Herpes viruses (HSV-1 and HSV-2); Varicella Zoster virus (VZV); and measles.

8 Claims, 8 Drawing Sheets

OTHER PUBLICATIONS

Aach, R. D. The treatment of chronic type B viral hepatitis. *Ann. Intern. Med.* 1988, 109, 89–91.

Alexander, G. J.; Brahm, J.; Fagan, E. A.; Smith, H. M.; Daniels, H. M.; Eddleston, A. L.; Williams, R., Loss of HBSAg with interferon therapy in chronic hepatitis B virus infection. *Lancet* 1987, ii, 66–69.

Arya, Ranjiana; Babu, Vikas; Ilyas, M.; Nasim, K.T. Phytochemical examination of the leaves of *Anaeardium occidentale*. *J. Indian Chem. Soc.*, 1989, 66, 67–68.

Anand, K.K.; Gupta, V.N.; Rangari, V.; Singh, B.; Chandan, B.K. Structure and hepatoprotective activity of a biflavonoid from *Ganarium manii*. *Planta Medica*, 1992, 58, 493–495.

Bardos, T.J.; Schinazi, R.F. Ling, K.–H.; Heider, A.R. Structure–activity relationships and mode of action of 5–mercapto–substituted oligo– and polynucleotides as antitemplates inhibiting replication of human immunodeficiency virus type 1. *Antimicrob. Agents Chemother.*, 1992, 36, 108–114.

Barre–Sinoussi, F.; Chermann, J.C.; Rey, R.; Nugeyre, L.M.T.; Chamaret, S.; Gruest, J.; Dauguet, C.; Axler–Blin, C.; Vezinet–Brun, F.; Rouzioux, C.; Rozenbaum, W., and Montagnier, L. Isolation of a T–lymphotopic retrovirus from a patient at risk for acquired immune deficiency syndrome (AIDS). *Science,* 1983, 220, 868–871.

Barron, D.; Ibrahim, R.K. Synthesis of flavanoid sulfates: 1. stepwise sulfation of position, 3, 7, and 4' using N,N'–dicyclohexycarbodiimide and tetrabutylamminium hydrogen sulfate. *Tetrahedron,* 1987, 43, 5197–5202.

Bryson, Y. J.; Monahan, C.; Pollack, M.; Shields, W. D. A prospective double–blind study of side effects associated with the administration of amantadine for influenza A virus prophylaxis. *J. Infect. Dis.* 1980, 141, 543–547.

Chen, F.C.; Lin, Y.M.; Hung, J.C. A new biflavanone glucoside from *Garcinia multiflora*. *Phytochemistry,* 1975C, 14, 818–820.

Chen, F.C.; Lin, Y.M.; Liang, C.M. Biflavonyls from drupes of *Rhus succedanea*. *Phytochemistry,* 1974A, 12, 276–277.

Chen, F.C.; Lin, Y.M. Rhusflavanone, a new biflavanone from the seeds of wax tree. *J. Chem. Soc., Perkin Trans.,* 1976, I, 98–101.

Chen, F.C.; Lin, Y.M. Succedaneaflavanone—A new 6,6—biflavanone from *Rhus succedanea*. *Phytochemistry,* 1975A, 14, 1644–1647.

Chen, F.C.; Lin Y.M.; Hung, J.G. Phenolic compounds from the heartwood of *Gracinia multiflora*. *Phytochemistry,* 1975B, 14, 300–303.

Cholbi, M.R.; Paya, M.; Alcaraz, M.J. Inhibitory effects of phenolic compounds on $CCl_4$ induced microsomal lipid peroxidation. *Experientia,* 1991, 47, 195–199.

Chou, T.–C.; Talalay, P. Quantitative analysis of dose–effect relationships: The combined effects of multiple drugs or enzyme inhibitors. *Adv. Enz. Regul.,* 1984, 22, 27–35.

Couch, R. B.; Jackson, G. G. Antiviral agents in influenza—Summary of influenza workshop VIII. *J. Infect. Dis.* 1976, 134, 516–527.

Degelau, J; Somani, S. K.; Cooper, S. L.; Guay, D. R. P.; Crossley, K. B. Amantadine–resistant influenza A in a nursing facility. *Arch. Intern. Med.* 1992, 152, 390–392.

Ono, K.; Nakane, H.; Jukushima, M.; Chermann, J.K.; Barre–Sinoussi, F. Inhibition of reverse transcriptase acitivity by a flavonoid compound, 5,6,7–trihydroxyflavone. *Biochem. Biophys. Res. Commu.,* 1989, 160, 982–987.

Dolin, R.; Reichman, R. C.; Madore, H. P.; Maynard, R.; Lindon, P. M.; Webber–Jones, J. A controlled trial of amantadine and rimandatine in the prophylaxis of influenza A infections. *N. Engl. J. Med.* 1982, 307, 580–584.

Doong, S. L.; Tsai, C. H.; Schinazi, R. F.; Liota, D. C.; Cheng, Y. C. Inhibition of the replication of hepatitis B virus in vitro by 2',3'–dideoxy–3'–thiacytidine and related analogues. *Pro. Natl. Acad. Sci. USA* 1991, 88, 8495–8499.

Gallo, R.C.; Salahuddin, S.Z.; Popovic, M.; Shearer, G.M.; Kaplan, M.; Haynes, B.F.; Palker, T.J.; Redfield, R.; Oleske, J.; Safai, B.; White, G.; Foster, P.; Markham, P.D. Frequent and detection and isolation of cytopathic retroviruses (HTLV–III) from patients with AIDS and at risk for AIDS. *Science,* 1984, 224,500–503.

Geiger, H.; Seeger, T.; Hahn, H.; Zinsmeister, H.D. 1H NMR Assignments in biflavanoid spectra by proton–detected C–H correlation. *Z. Naturforsch,* 1993, 48c, 821–826.

Hayashi, T.; Morita, N. Mechanism of action of the antiherpesvirus biflavone ginkgetin. *Antimicrob. Agents Chemother.,* 1992, 36, 1890–1893.

Hayden, F. G.; Belshe, R. B.; Clover, R. D.; Hay, A. J.; Oakers, M. G.; Soo, W. Emergence and apparent transmission of rimantadine–resistant influenza virus in families. *N. Engl. J. Med.* 1989, 321, 1696–1702.

Hoffmann, C. E. Amantadine HC1 and related compounds. In *Selective Inhibitors of Viral Functions;* Carter, W. A., Ed.; CRC Press: Cleveland, 1973, 199–211.

Hoofnagle, J. H. Chronic hepatitis B, *N. Engl. J. Med.* 1990, 323, 337–339.

Huang, L.; Kashiwade, Y.; Cosentino, L.M.; Fan, S.; Chen, C.H.; McPhail, A.T.; Fujoika, T.; Mihasha, K.; and Lee, K.H. Anti–AIDS Agents. 15. Synthesis and Anti–HIV Activity of Dihydroseselins and Related Analogs. *J. Med. Chem.,* 1994, 37, 3947–3955.

Iwu, M.M.; Igbokao, O.A.; Onwuchekwa, U.A; Okunii, C.O. Evaluation of the antihepatotoxic activity of the biflavonoids of Garcinia kola seed. *J. Ethnopharmacol.,* 1987, 21, 127–138.

Kimberlin, D. W.; Crampacker, C. S.; Straus, S. E.; Biron, K. K.; Drew, W. L.; Hayden, F. G.; McKinlay, M.; Richman, D. D.; Whitley, R. J. Antiviral resistance in clinical practice. *Antiviral Res.,* 1995, 26, 423–438.

Knight, V.; Gilbert, B. E. Ribavirin aerosol treatment of influenza. In *Infectious Disease Clinics of North America,* vol. 1; Moellering, Jr.. Ed.; 1987, 441–457.

Konoshima, T.; Takasaki, M.; Kozuka, M.; Lin, Y.M.; Chen, F.C.; Tokuda, H.; Matsumoto, T. Studies on inhibitors of skin tumors promotion (IV). Inhibitory effects of flavonoids on Epstein–Barr virus activation (1). *Shoyakugaku Zasshi,* 1988, 42, 343–346.

Korba, B.E.; Milman, G. A cell culture assay for compounds which inhibit hepatitis B virus replication *Antiviral Res.,* 1991, 15, 217–228.

Korba, B.E.; Gerin, J.L. Use of a standardized cell culture assay to assess activities of nucleoside analogs against hepatitis B virus replication. *Antiviral Res.,* 1992, 19, 55–70.

Korba, B.E.; Gerin, J.L. Antisense oligonucleotides are effective inhibitors of hepatitis B virus replication in vitro. *Antiviral Res.,* 1995, 28, 225–242.

Li–zhen, X.; Chem, Z.; sun, N. Studies of Chemical Compositions of *Podocarpus nerifolius* D. Don. *Zhiwu Xuebao,* 1993, 35, 138–143.

Lin, Y.M.; Chen, F.C. Agathisflavone from the drupes of *Rhus succedanea*. *Phytochemistry,* 1974B, 13, 657–658.

Lopez–Saez, J.A.; Perez–Alonso, M.; Negueruela, A.V. Biflavanoids of *Selaginella denticulata* growing in Spain. *Naturforsch.*, 1994, 49c, 267–270.

Magri, N.J.; Kinston, D.G. I. Modified Toxols, 4. Synthesis and biological activity of toxols modified in the side chain. *J. Nat. Prod.*, 1987, 51, 298–306.

Markham, K.R.; Sheppard, C.; Geiger, H. $^{13}$C NMR studies of some naturally occurring amentoflavone and hinokiflavone biflavanoids. *Phytochemistry*, 1987, 26, 3335–3337.

Martin, P. and Friedman, L. S. In *Innovations in Antiviral Development and the Detection of Virus Infections*; T. M. Block; D. Junkind; R. L. Crowell; M. Dension; L. R. Walsh, Ed.; Plenum Press: New York, 1992, 111–120.

Mast, E. E.; Harmon, M. W.; Graventstein, S.; Wu, S. P.; Arden, H. H.; Circo, R.; Tyszka, G.; Kendal, A. P.; Davis, J. P. Emergence and possible transmission of amantadine–resistant viruses during nursing home outbreaks of influenza A (H3N2). *Am J. Epidemiol.* 1992, 134, 988–997.

McDougal, J.S.; Cort, S.P.; Kennedy, M.S.; Cabridilla, C.D.; Feorino, P.M.; Francis, D.P.; Hicks, K.; Kalyanaramen, V.S.; Martin, L.S. Immunoassay for the detection and quantitation of infectious human retrovirus, lymphadenopathy–associated virus (LAV). *J. Immun. Meth.* 1985, 76, 171–183.

Mora, A.; Paya, M.; Roips, K. Structure–activity relationships of polymethoxyflavones and other flavonoids as inhibitor of non–enzymatic lipid peroxidation. *Biochem–Pharmacol.*, 1990, 40, 793–797.

Muller, C.; Bergmann, K.F.; Gerin, J.L.; Korba, B.E. Production of hepatitis B virus by stably transfected monocytic cell line U–937: a model for extrahepatic hepatitis B virus replication. *J. Infect. Dis.*, 1992, 165, 929–933.

Murakami, A.; Ohigashi, H.; Jisaka, M.; Irie, R.; Koshimizu, K. Inhibitory effects of new types of biflavonoid–related polyphenols; lophirone A and lophiraic acid, on some tumor promoter–induced biological responses in vitro and in vivo. *Cancer Lett.* (Shannon, Irel.), 1991, 58, 101–106.

Nagai, T.; Miyaichi, Y.; Tomimori, T.; Suzuki, Y.; Yamada, N. Inhibition of influenza virus sialidase and anti–influenza virus activity by plant flavonoids. *Chem. Pharm. Bull.*, 1990, 38, 1329–1332.

Nagai, T.; Miyaichi, Y.; Tomimore, T.; Suzuki, Y.; Yamada, H. In vivo anti–influenza virus activity of plant flavonoids possessing inhibitory activity for influenza virus sialidase. *Antiviral Res.*, 1990, 19: 207–217.

Nagai, T.; Suzuki, Y.; Tomimore, T.; Yamada, H. Antiviral activity of plant flavonoid, 5,7,4'–trihydroxy–8–methoxyflavone, from roots of *Scutellaria baicalenais* against influenza A (H3N2) and B viruses. *Biol. Phar. Bull.*, 1995, 18, 295–299.

Nagai, T.; Moriguchi, R.; Suzuki, Y.; Tomimori, T.; Yamada, H. Mode of action of the anti–influenza virus activity of plant flavonoid, 5,7,4'–trihydroxy–8–methoxyflavone, form the roots of *Scutellaria baicalensis*. *Antiviral Res.*, 1995, 26, 11–25.

Nakazawa, K. Chemical structure of ginkgetin. Gifu Yakka Diagaku. Kiyo, 1941, 12, 1, *Chem. Abst.* 59, 2759d.

Ono, K.; Nakane, H.; Jukushima, M.; Chermann, J.K.; Barre–Sinlussi, F. Differential inhibitory effects of various flavonoids on the activities of reverse transcriptase and cellular DNA and RNA polymerases. *Euro. J. Biochem.*, 1990, 190, 469–476.

Qasim, M.A.; Roy, S.K.; Ilyas, M. Phenolic Constituents of Selaginellaceae. *Indian Journal of Chemistry* 1985, 24B, 220.

Ray, C. G.; Icenogle, T. B.; Minnich, L. L; Copeland, J. G.; Grogan, T. M. The use of intravenous ribavirin to treat influenza virus–associated acute myocarditis. *J. Infect Dis.*, 1989, 159, 829–836.

Sanz, M.J.; Ferrandiz, M.J.; Cejudo, M.; Terencia, M.C.; Gil, B.; Bustos, G.; Ubeda, A.; Gunasegaran, R.; Alcaraz, M.M. Influence of a series of natural flavonoids on free radical generating systems and oxidative stress. *J. Xenobiotica*, 1994, 24, 689–699.

Schinazi, R.F.; Cannon, D.L.; Arnold, B.H.; Martino–Saltzman, D. Combination of isoprinosine and 3'–azido–3'–deoxythymidine in lymphocytes infected with human immunodeficiency virus type 1. *Antimicrob. Agents Chemother.*, 1988, 32, 1784–1787.

Schinazi, R.F.; Sommadossi, J.P.; Saalmann, V.; Cannan, M.W.; Hart, G.; Smith, G.; Hahn, E. Activity of 3'–azido–3'–deoxythimidine nucleotide dimmers in primary lymphocytes infected with human immunideficiency virus type 1. *Antimicrob. Agents Chemother.*, 1990, 34, 1061–1067.

Sidwell, R.W., Bailey, D.W.; Wong, M.H.; Huffman, J.H.; In vitro and in vivo sensitivity of a non–mouse–adapted influenza (Beijing) virus infection to amantadine and ribavirin. *Chemotherapy*, 1995: 41, 455–461.

Sidwell, R.; Huffman, R.; Gilbert. B.; Moscon, G.; Pedersen, R.; Burger, R.,; Warren, R. Utilization of pulse oximetry for the study of the inhibitory effects of antiviral agents on influenza virus in mice. *Antimicrob. Ag. Chemother.*, 1992, 36, 473–476.

Silva, G.L., Chai, H.; Gupta, M.P.; Farnsworth, N.R.; Cordell, G.A.; Pezzuto, J.M.; Beecher, C.W.W.; Kinghorn, A.D. Cytotoxic biflavanoids from *Selaginella willdenowii*. *Phytochemistry*, 1995, 40, 129–134.

Spira, T.J.; Bozeman, L.H.; Holman, R.C.; Warfield, K.T.; Phillips, S.K.; Feoprino, P.M. Micromethod for assaying the reverse transcriptase of LAV–HTIV–III/lymphadenopathy–associated virus. *J. Clin. Microbiol.*, 1987, 25, 97–99.

Tan, G.T.; Pezzuto, J.M.; Kinghorn, A.D. Evaluation of natural products as inhibitors of human immunodeficiency virus type 1 (HIV–1) reverse transcriptase. *J. Nat. Prod.*, 1991, 54, 143–154.

Tisdale, M.; Bauer, D. J. The relative potencies of anti–influenza compounds. *Ann. N. Y. Acad. Sci.* 1977, 284, 254–263.

Tsunoda, A.; Maasab, H. H.; Cochran, K. W.; Eveland, W. C. Antiviral activity of α–methyl–1–adamantane methylamine hydrochloride. *In Antimicrob. Agents Chemother.* 1966, 553.

van Leeuwen R.; Katlama, C.; Kitchen, V.; Boucher, C. A. B.; Tubiana, R.; McBride, M.; Ingrand, D.; Weber, J.; Hill, A.; McDade, H.; Danner, S. A. Evaluation of safety and efficacy of 3TC (Lamivudine) in patients with asymptomatic or mildly symptomatic human immunodeficiency virus infection: A phase I/II study. *J. Inf. Dis.* 1995, 171, 1166–1171.

Yokosuka, O.; Omata, O. M.; Imazeki, F.; Summers, J. Changes of hepatitis B virus DNA in liver and serum caused by recombinant leukocyte interferon treatment: analysis of intrahepatic replicative hepatitis B virus DNA. *Hepatology* 1985, 5, 728–734.

Lin et al., Phytochemistry, 13(8), 1617–19, Aug. 1974.

Lin et al., Planta Med., 55, 166–8, 1988.

* $P < 0.05$, ** $P < 0.01$ compared to DMSO-treated control

BIFLAVANOIDS AND DERIVATIVES THEREOF AS ANTIVIRAL AGENTS

CROSS-REFERENCE

This application is a divisional of U.S. application Ser. No. 08/668,284, filed Jun. 21, 1996, now U.S. Pat. No. 5,773,462, which is a continuation-in-part of U.S. provisional application Ser. No. 60/000,465, filed Jun. 23, 1995.

FIELD OF THE INVENTION

The present invention relates to substantially pure antiviral biflavanoids, e.g., robustaflavone, biflavanoid derivatives and salts thereof such as esters, ethers, amines, sulfates, ethylene oxide adducts, and acid salts, and pharmaceutical compositions containing the same. The present invention also relates to method for extracting substantially pure robustaflavanone from plant material. The present invention also relates to a method for preventing and/or treating viral infections such as hepatitis B, influenza A and B, and HIV.

BACKGROUND OF THE INVENTION

Viruses, an important etiologic agent in infectious disease in humans and other mammals, are a diverse group of infectious agents that differ greatly in size, shape, chemical composition, host range, and effects on hosts. After several decades of study, only a limited number of antiviral agents are available for the treatment and/or prevention of diseases caused by viruses such as hepatitis B, influenza A and B and HIV. Because of their toxic effects on a host, many antiviral agents are limited to topical applications. Accordingly, there is a need for safe and effective antiviral agents with a wide-spectrum of anti-viral activity with reduced toxicity to the host.

Since the identification of the human immunodeficiency virus (HIV) as the causative agent of AIDS,[36,46] the search for safe and effective treatments for HIV infection has become a major focus for drug discovery groups around the world. Investigations into the molecular processes of HIV have identified a number of macromolecular targets for drug design, such as HIV-1 reverse transcriptase (HIV-RT), protease and integrase enzymes, and regulatory proteins (e.g., TAT and REV). Other targets are enzymes which aid in virus attachment and fusion. HIV-RT is an essential enzyme in the life cycle of HIV, which catalyzes the transcription of HIV-encoded single-stranded RNA into double-stranded DNA. Furthermore, the RNA-dependent DNA polymerase function of HIV-RT does not have an analogous process in mammalian metabolism, and thus is a suitable target for a chemotherapeutic agent.

The hepatitis B virus (HBV) infects people of all ages. It is one of the fastest-spreading sexually transmitted diseases, and also can be transmitted by sharing needles or by behavior in which a person's mucus membranes are exposed to an infected person's blood, semen, vaginal secretions, or saliva. While the initial sickness is rarely fatal, ten percent of the people who contract hepatitis are infected for life and run a high risk of developing serious, long-term liver diseases, such as cirrhosis of the liver and liver cancer, which can cause serious complications or death.[1] The World Health Organization lists HBV as the ninth leading cause of death. It is estimated that about 300 million persons are chronically infected with HBV worldwide, with over 1 million of those in the United States. The Center for Disease Control estimates that over 300,000 new cases of acute HBV infection occurs in the United States each year, resulting in 4,000 deaths due to cirrhosis and 1,000 due to hepatocellular carcinoma.[2] The highest rates of HBV infections occur in Southeast Asia, South Pacific Islands, Sub-Saharan Africa, Alaska, Amazon, Bahai, Haiti, and the Dominican Republic, where approximately 20% of the population is chronically infected.[3]

Hepatitis B virus (HBV) infection is currently the most important chronic virus infection, but no safe and effective therapy is available at present. The major therapeutic option for carriers of HBV is alpha interferon, which can control active virus replication. However, even in the most successful studies, the response rate in carefully selected patient groups has rarely exceeded 40%.[5,6] One of the reasons cited for interferon failure is the persistence of viral supercoiled DNA in the liver.[7] Clinical exploration of many promising antiviral agents such as nucleoside analogues is hampered because their aspecific body distribution leads to significant toxic side effects. Recently, however, a new nucleoside analogue, 2',3'-dideoxy-3'-thiacytidine (3TC), was discovered and found to be extremely potent against HBV replication with only minimal side effects.[8-10]

Influenza is a viral infection marked by fever, chills, and a generalized feeling of weakness and pain in the muscle, together with varying signs of soreness in the respiratory tract, head, and abdomen. Influenza is caused by several types of myxoviruses, categorized as groups A, B, and $C_4$. These influenza viruses generally lead to similar symptoms but are completely unrelated antigenically, so that infection with one type confers no immunity against the other. Influenza tends to occur in wavelike epidemics throughout the world; influenza A tends to appear in cycles of two to three years and influenza B in cycles of four to five years. Influenza is one of the few common infectious diseases that are poorly controlled by modern medicine. Its annual epidemics are occasionally punctuated by devastating pandemics. For example, the influenza pandemic of 1918, which killed over 20 million people and affected perhaps 100 times that number, was the most lethal plague ever recorded. Since that time, there have been two other pandemics of lesser severity, the so-called Asian flu of 1957 and the Hong Kong flu of 1968. All of these pandemics were characterized by the appearance of a new strain of influenza virus to which the human population had little resistance and against which previously existing influenza virus vaccines were ineffective. Moreover, between pandemics, influenza virus undergoes a gradual antigenic variation that degrades the level of immunological resistance against renewed infection.[4]

Anti-influenza vaccines, containing killed strains of types A and B virus currently in circulation, are available, but have only a 60 to 70% success rate in preventing infection. The standard influenza vaccine has to be redesigned each year to counter new variants of the virus. In addition, any immunity provided is short-lived. The only drugs currently effective in the prevention and treatment of influenza are amantadine hydrochloride and rimantadine hydrochloride.[11-13] While the clinical use of amantadine has been limited by the excess rate of CNS side effects, rimantadine is more active against influenza A both in animals and human beings, with fewer side effects.[14,15] It is the drug of choice for the chemoprophylaxis of influenza A.[13,16,17] However, the clinical usefulness of both drugs is limited by their effectiveness against only influenza A viruses, by the uncertain therapeutic efficacy in severe influenza, and by the recent findings of recovery of drug-resistant strains in some treated patients.[18-22] Ribavirin has been reported to be therapeutically active, but it remains in the investigational stage of development.[23,24]

While the search for viable therapeutics for treatment of both HBV and influenza infections has been moderately successful, therapeutic agents for HIV are severely limited. Furthermore, there are no known safe and therapeutic treatments for HBV, influenza and HIV. In HBV, with the possible exception of the drug 3TC, the use of nucleoside-based antiviral agents leads to toxicity, probably due to cross-inhibition of cellular mitchondrial DNA. Clearly, there is a need for a new class of antiviral agents which could minimize the toxicity associated with cross-inhibition. In influenza, amantadine and rimantadine have been shown to be moderately effective against only influenza A viruses; with amantadine having excessive side effects. Recently, strains of influenza A resistant to amantadine and rimantadine have been isolated. Accordingly, there is a need for new types of therapeutic antiviral agents against both influenza A and influenza B, as well as against HBV and HIV.

SUMMARY OF THE INVENTION

The present invention relates to substantially purified antiviral biflavanoids, derivatives and salts thereof and pharmaceutical compositions containing the same; an improved method for extracting substantially pure robustaflavonone from plant material; methods for preparing derivatives and salts from antiviral biflavanoids; and methods for treating and/or preventing viral infections using the antiviral biflavanoids, derivatives and salts thereof.

The present invention provides substantially purified biflavanoids comprising robustaflavone, hinokiflavone, amentoflavone, agathisflavone, morelloflavone, volkensiflavone, rhusflavanone, succedaneaflavanone, GB-1a, and GB-2a and pharmaceutical compositions containing the same are disclosed. Scheme I illustrates the chemical structures of these biflavanoids. The biflavanoids of the invention, extractable from from plant materials derived from a variety of natural sources such as *Rhus succedanea* and *Garcinia multiflora,* were found to be effective in inhibiting viral activity and may be used in a method for treating and/or preventing a broad range of viral infections such as Influenza A and B, hepatitis B and HIV-1, HSV-1, HSV-2, VZV, and measles. It has been discovered that robustaflavone effectively inhibits activity of influenza A and B viruses, hepatitis B, HIV-1, HSV-1 and HSV-2. Hinokiflavone and morelloflavone exhibited similar activity against various strains of HIV-1.

Anti-viral biflavanoid derivatives and salts and pharmaceutical compositions containing the same are also contemplated by the invention. Representative derivatives include ethers, e.g., methyl ethers, esters, amines, ethylene oxide adducts, and polymers such as trimers and tetramers of apeginin. Representative salts include sulfates and acid salts. Methods for preparing these derivatives and salts are also provided. It has been discovered for instance that salts of robustaflavone, e.g., robustaflavone tetrasulfate potassium salt, effectively inhibits hepatitis B activity. Scheme I illustrates several examples of biflavanoid derivatives.

An improved method for extracting robustaflavone from plant material is also provided. According to this method, a substantially pure robustaflavone in greater yields can be obtained through the use of a particular solvent mixture comprising toluene/ethanol/pyridine. The improved extraction method eliminates the use of benzene and requires smaller volumes of pyridine from the prior reported methods.

Finally, a method for treating and/or preventing viral infections using antiviral biflavanoids is described. Representative viral infections include influenza A and B viruses, hepatitis B and human immunodeficiency virus (HIV-1), HSV-1, HSV-2, VZV, and measles.

Accordingly, it is an object of the invention to provide substantially purified antiviral biflavanoids robustaflavone, hinokiflavone, amentoflavone, agathisflavone, morelloflavone, rhusflavanone, succedaneaflavanone, GB-1a, and GB-2a.

It is another object of the invention to provide antiviral derivatives and salt forms of biflavanoids robustaflavone, hinokiflavone, amentoflavone, agathisflavone, morelloflavone, volkensiflavone, rhusflavanone, succedaneaflavanone, GB-1a, and GB-2a as well as method of preparation thereof. A representative example of an antiviral biflavanoid derivative includes robustaflavone tetrasulfate potassium salt.

It is yet another object of the invention to provide pharmaceutical compositions which include at least one antiviral biflavanoids such as robustaflavone, hinokiflavone, amentoflavone, agathisflavone, morelloflavone, volkensiflavone, rhusflavanone, succedaneaflavanone, GB-1a, GB-2a, derivatives or salts thereof.

It is a further object of the invention to provide an improved method for obtaining substantially pure robustaflavone and in greater yields than prior procedures.

It is yet a further object of the invention to provide a method for treating and/or preventing viral infections which comprises administering an antivirally effective amount of a biflavanoid. Representative viral infections are caused by viral agents such as influenza, e.g., influenza A and B; hepatitis, e.g., hepatitis B; human immunodeficiency virus, e.g., HIV-1; HSV-1, HSV-2, VZV, and measles.

These and other objects of the invention will become apparent in light of the detailed description below.

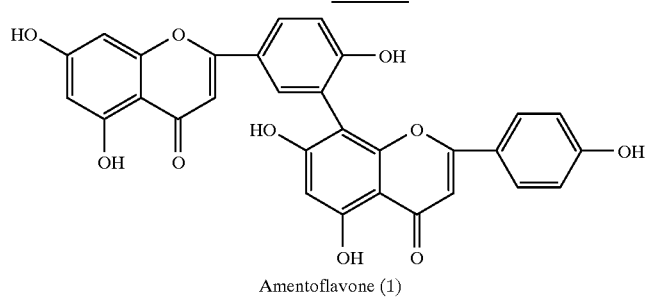

Scheme I

Amentoflavone (1)

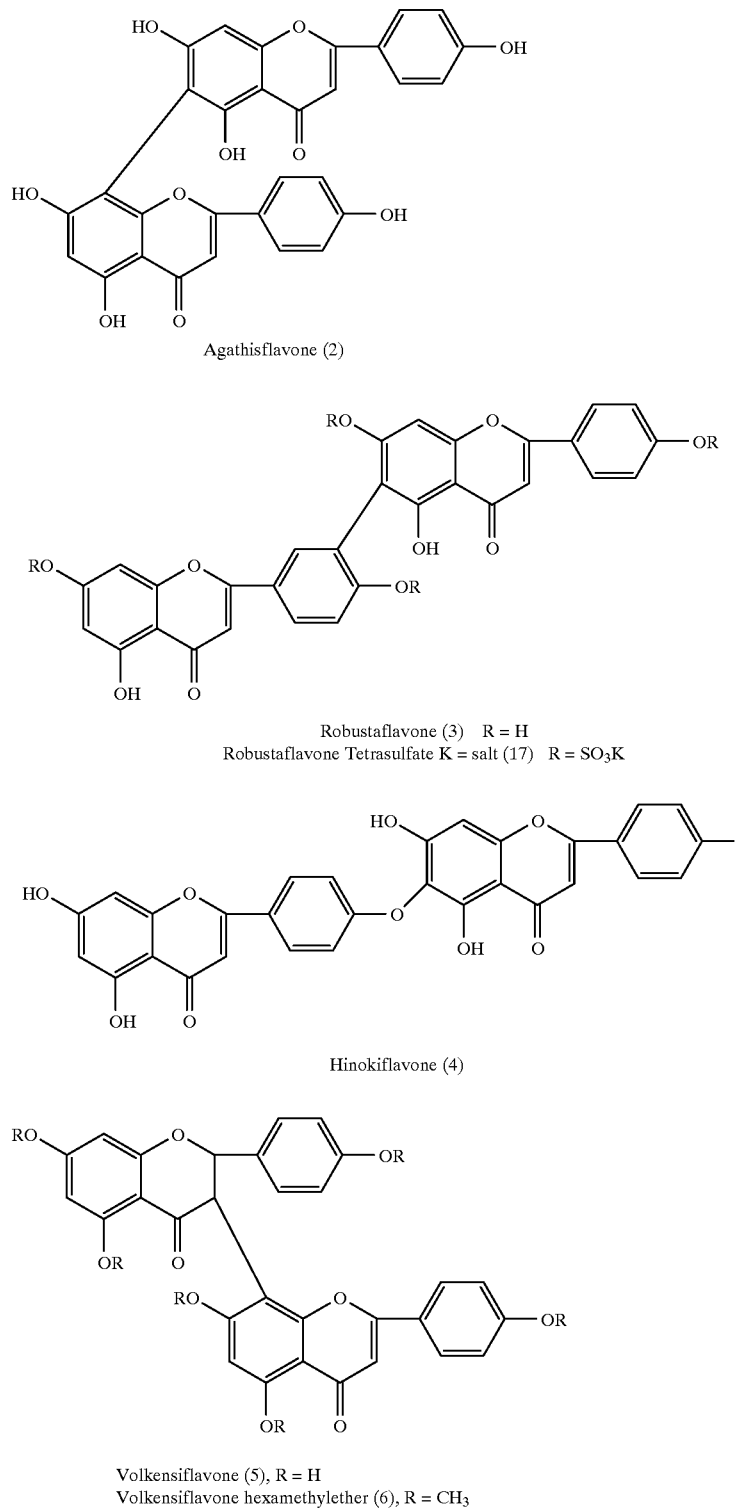
Agathisflavone (2)
Robustaflavone (3)  R = H
Robustaflavone Tetrasulfate K = salt (17)  R = SO$_3$K
Hinokiflavone (4)
Volkensiflavone (5), R = H
Volkensiflavone hexamethylether (6), R = CH$_3$

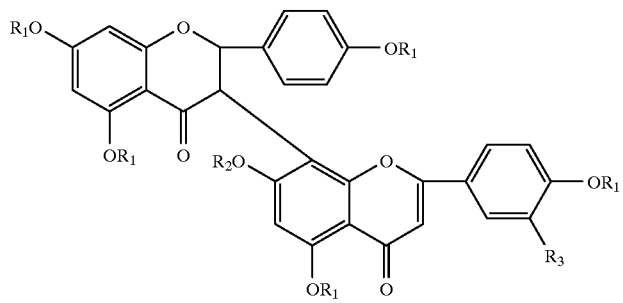
Morelloflavone (7), $R_1 = R_2 = H$, $R_3 = OH$
Morrelloflavone heptamethyl ether (8), $R_1 = R_2 = CH_3$, $R_3 = OCH_3$
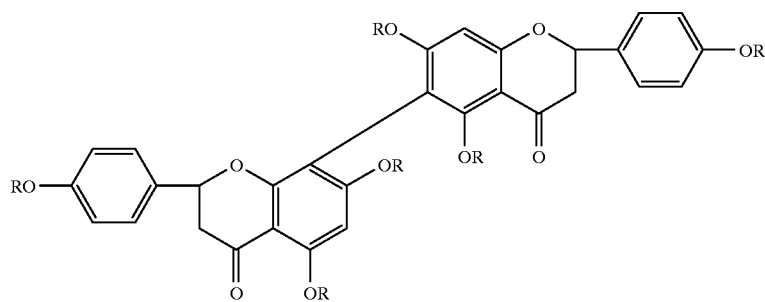
Rhusflavanone (9), R = H
Rhusflavanone hexaacetate (10), $R = COCH_3$
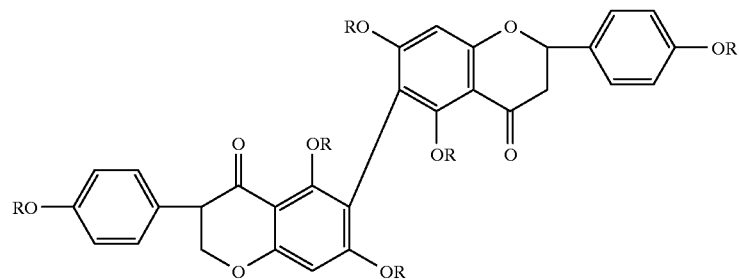
Succedaneaflavanone (11), R = H
Succedaneaflavanone hexaacetate (12), $R = COCH_3$
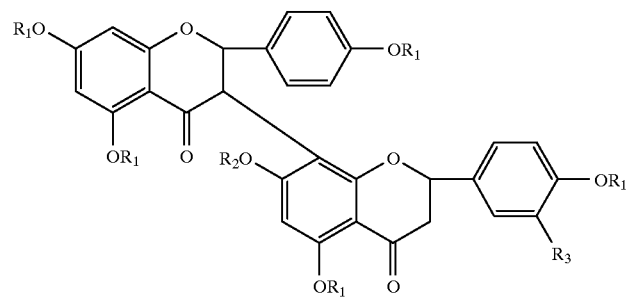
GB-1a (13), $R_1 = R_2 = R_3 = H$
GB-1a hexamethyl ether (14), $R_1 = R_2 = CH_3$, $R_3 = H$
GB-1a glucoside (16), $R_1 = R_3 = H$, $R_2 = Glc$
GB-2a (16), $R_1 = R_2 = H$, $R_3 = OH$

DETAILED DESCRIPTION OF THE INVENTION

Figure 1:
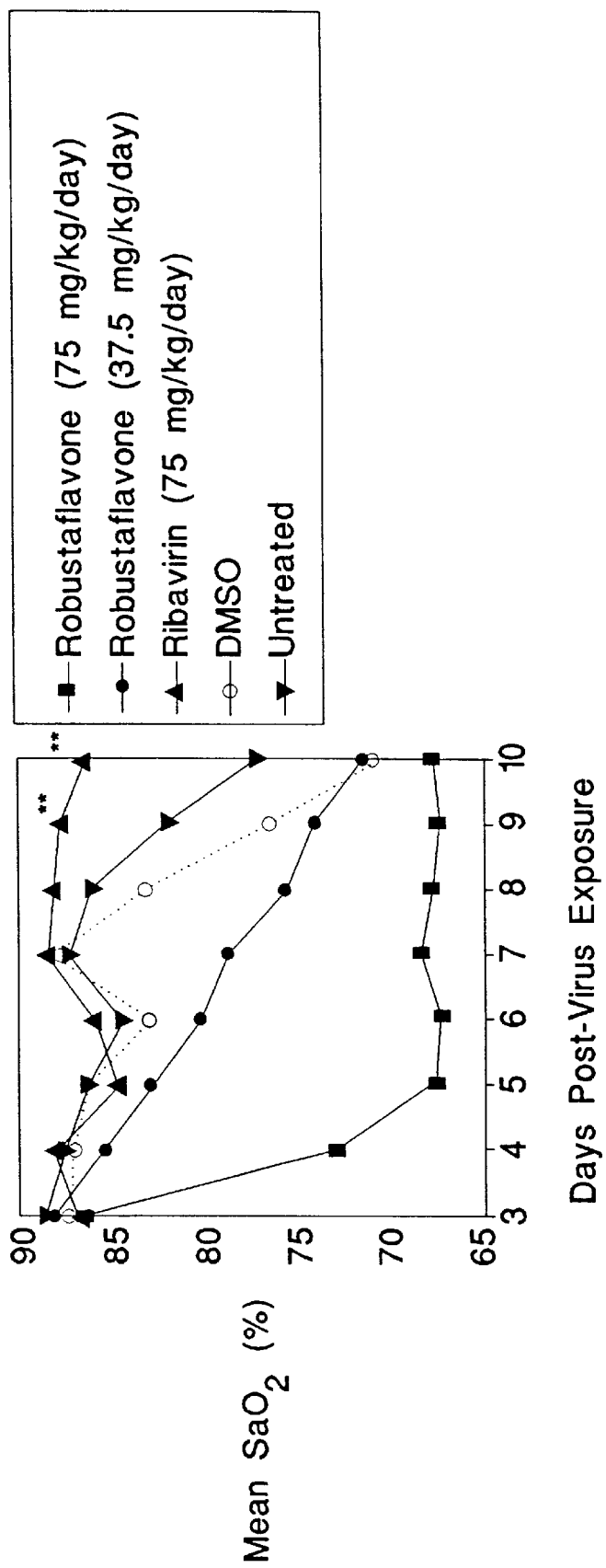
FIG. 1 illustrates the effect of treatment with robustaflavone in DMSO on mean arterial oxygen saturation (mean $SaO_2$ (%)) in Influenza A virus-infected mice as described in Example 10.

All references and patents cited herein are hereby incorporated by reference in their entirety.

In one embodiment of the invention, substantially pure biflavanoids robustaflavone, hinokiflavone, amentoflavone, agathisflavone, morelloflavone, volkensiflavone, rhusflavanone, succedaneaflavanone, GB-1a, and GB-2a, derivatives and salts of the biflavanoids, and pharmaceutical compositions containing the same are disclosed. Methods for extracting and isolating the biflavanoids were previously reported.[28,37,39,40,53–55] Moreover, methods for preparing derivatives such as the acetate[37,38] and methyl ethers[39,40] for several of these biflavanoids are also reported. Representative methods for preparing biflavanoid derivatives are illustrated in the examples below. Applicants have determined that these biflavanoids, especially robustaflavone, were surprisingly effective in inhibiting one or more activities of viruses such as Influenza A and B, hepatitis B and HIV-1, HSV-1, HSV-2, VZV, and measles.

Approximately 100 biflavanoids have been isolated to date, since the first biflavanoid, a biflavone, was isolated in 1929 by Furukawa from ginkgo biloba L. as a yellow pigment.[44,45,61] Biological activities of several biflavanoids, such as ginkgetin, have been reported. For instance, peripheral vasodilatation, anti-bradykinin, and anti-spasmogenic activities have been observed.[48,62] Garcinikolin stimulates RNA synthesis in rat hepatocyte suspensions.[57] Also, agathisflavone, kolaviron, GB-1 and GB-2 have hepatoprotective activity.[33,49] Hinokiflavone, kayaflavone, bilobetin, lophirone A, lophiraic acid, and sotetusflavone demonstrate inhibitory action on the genome expression of the Epstein-Barr virus (EBV).[51,52,60] GB-1 exhibits molluscicidal activity,[65] while daphnodorin A, daphnodorin B, and daphnodorin D possess antimicrobial activity.[34] Hinokiflavone exhibits cytotoxicity against tissue cultured cells of human mouth epidermoid carcinoma (KB).[56] Amentoflavone and morelloflavone exhibit an inhibitory effect on lipid peroxidation,[41,59,66] and kolaviron produced hypoglycemic effects.[50] None of these references, however, disclose or suggest that robustaflavone, hinokiflavone, morelloflavone, amentoflavone, agathisflavone, volkensiflavone, rhusflavanone, succedaneaflavanone, GB-1a and GB-2a, especially robustaflavone and its tetrasulfate potassium salt, have an inhibitory effect against at least one of influenza, e.g., influenza A and B; hepatitis, e.g., hepatitis B; human immunodeficiency virus, e.g., HIV-1; HSV-1, HSV-2, VZV, and measles.

In another embodiment of the invention, an improved method for extracting substantially pure robustaflavone from natural sources is also provided. Robustaflavone, 1, a naturally occurring biflavanoid, was previously isolated, purified, and identified from the seed-kernels of *Rhus succedanea*.[25] Other sources of robustaflavone include: seed kernel of *Rhus succedanea* L.;[25] leaves of *Selaginella lepidophylla*;[27] leaves of *Anacardium occidentale*;[28] leaves and branches of *Podocarpus neriifolius* D. Doa;[29] *Selaginella denticulata*;[30] and *Selaginella willdenowii*.[31]

The drupes of wax-tree, *Rhus succedanea* L (Anacardiaceae), are of great economic importance in that they yield Japan wax. Earlier work on this species has shown the presence of fustin and fisetin in the wood, rhoifolin in leaves, japanic acid in the wax, and ellagic acid, fatty acids, and flavanoids in the seed kernels. Further studies of the pigment in the seed kernels of wax-tree led to the isolation of eight biflavanoids, four of which were new. Concentration of the ethanol extract of the seed kernels yielded, successively, fractions of ellagic acid, pigment A (hinokiflavone and robustaflavone) and pigment B (amentoflavone). Further concentrations gave a crude yellow pigment C which, when subjected to silica gel column chromatography, afforded fractions $C_I$ (rhusflavanone, succedaneaflavanone and neorhusflavanone), $C_{II}$ (rhusflavone), and $C_{III}$ (agathisflavone).

A prior method for extracting and isolating substantially pure robustaflavone from plant material was reported.[55] This method, however, used large quantities of benzene and pyridine which is undesirable for use in large scale extractions and produced mediocre yields of robustaflavone. The applicants discovered an improved extraction method which eliminates benzene and greatly reduced the amount of pyridine and produced at least double the quantities of substantially pure robustaflavone compared to the prior method. According to this embodiment of the invention, a solvent mixture comprising toluene/ethanol/formic acid at a volume ratio ranging about 10–30:2–10:1, preferably about 20:5:1, was found to be useful. This particular solvent mixture was found to be especially useful in large scale extractions. An example of an extraction via the improved extraction method of the invention is illustrated in the examples below.

In yet another embodiment of the invention, a method for treating and/or preventing viral infections in mammals comprising administering an antivirally effective amount of a biflavanoid such robustaflavone, hinokiflavone, amentoflavone, agathisflavone, morelloflavone, volkensiflavone, rhusflavanone, succedaneaflavanone, GB-1a, and GB-2a. In practicing this invention, administration of robustaflavone or derivatives thereof is preferred. Examples of mammals include humans, primates, bovines, ovines, porcines, felines, canines, etc. Examples of viruses may include, but not be limited to, HIV-1, HIV-2, herpes simplex virus (type 1 and 2) (HSV-1 and 2), varicella zoster virus (VZV), cytomegalovirus (CMV), papilloma virus, HTLV-1, HTLV-2, feline leukemia virus (FLV), avian sarcoma viruses such as rous sarcoma virus (RSV), hepatitis types A–E, equine infections, influenza virus, arboviruses, measles, mumps and rubella viruses. More preferably the compounds of the present invention will be used to treat a human infected with hepatitis and/or influenza virus. Preferably the compounds of the present invention will also be used to treat a human exposed or infected (i.e., in need of such treatment) with the human immunodeficiency virus, either prophylactically or therapeutically.

Antiviral biflavanoids and derivatives thereof may be formulated as a solution of lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, standard 5% dextrose in water or in buffered sodium or ammonium acetate solution. Such formulation is especially suitable for parenteral administration, but may also be used for oral administration. It may be desirable to add excipients such as polyvinylpyrrolidone, gelatin, hydroxy cellulose, acacia, polyethylene glycol, mannitol, sodium choride or sodium citrate.

Alternatively, the compounds of the present invention may be encapsulated, tableted or prepared in an emulsion (oil-in-water or water-in-oil) syrup for oral administration. Pharmaceutically acceptable solids or liquid carriers, which are generally known in the pharmaceutical formulary arts, may be added to enhance or stabilize the composition, or to facilitate preparation of the composition. Solid carriers include starch (corn or potato), lactose, calcium sulfate dihydrate, terra alba, croscarmellose sodium, magnesium stearate or stearic acid, talc, pectin, acacia, agar, gelatin, maltodextrins and microcrystalline cellulose, or collodial silicon dioxide. Liquid carriers include syrup, peanut oil, olive oil, corn oil, sesame oil, saline and water. The carrier may also include a sustained release material such as glyceryl monostearate or glyceryl distearate, alone or with a wax. The amount of solid carrier varies but, preferably, will be between about 10 mg to about 1 g per dosage unit.

The dosage ranges for administration of biflavanoids or derivatives thereof are those which produce the desired affect whereby symptoms of infection are ameliorated. For example, as used herein, a pharmaceutically effective amount for influenza or hepatitis infection refers to the amount administered so as to maintain an amount which suppresses or inhibits circulating virus throughout the period during which infection is evidenced such as by presence of anti-viral antibodies, presence of culturable virus and presence of viral antigen in patient sera. The presence of anti-viral antibodies can be determined through use of standard ELISA or Western blot assays for example. The dosage will generally vary with age, extent of the infection, the body weight and counterindications, if any, for example, immune tolerance. The dosage will also be determined by the existence of any adverse side effects that may accompany the compounds. It is always desirable, whenever possible, to keep adverse side effects to a minimum.

One skilled in the art can easily determine the appropriate dosage, schedule, and method of administration for the exact formulation of the composition being used in order to achieve the desired effective concentration in the individual patient. However, the dosage can vary from between about 0.001 mg/kg/day to about 150 mg/kg/day, but preferably between about 1 to about 50 mg/kg/day.

The pharmaceutical composition may contain other pharmaceuticals in conjunction with biflavanoids and derivatives thereof to treat (therapeutically or prophylactically) antiviral infections. For example, other pharmaceuticals may include, but are not limited to, other antiviral compounds (e.g., AZT, ddC, ddI, D4T, 3TC, acyclovir, gancyclovir, fluorinated nucleosides and nonnucleoside analog compounds such as TIBO derivatives, nevirapine, saquinavir, α-interfon and recombinant CD4), immunostimulants (e.g., various interleukins and cytokines), immunomodulators and antibiotics (e.g., antibacterial, antifungal, anti-pneumocysitis agents).

The following examples are illustrative and do not serve to limit the scope of the invention as claimed. In these examples, eleven biflavanoids, amentoflavone (1), agathisflavone (2), robustaflavone (3), hinokiflavone (4), volkensiflavone (5), morelloflavone (7), rhusflavanone (9), succedaneaflavanone (11), GB-1a (13), GB-1a 7"-O-β-glucoside (15), and GB-2a (16), isolated from *Rhus succedanea* and *Garcinia multiflora,* and their methyl ethers, acetate and sulfate potassium salt, volkensiflavone hexamethyl ether (6), morelloflavone heptamethyl ether (8), rhusflavanone hexaacetate (10) succedaneaflavanone hexaacetate (12), GB-1a hexamethyl ether (14) and robustaflavone tetrasulfate potassium salt were evaluated for their antiviral activities. The inhibitory activities against HIV-1 RT and various viruses including herpes viruses (HSV-1, HSV-2, HCMV, and VZV), and respiratory viruses (influenza A, influenza B, RSV, parainfluenza 3, adenovirus 5, and measles) were investigated.

EXAMPLE 1

Extraction and Isolation of Biflavanoids

Isolation of Compounds

Compounds tested were isolated from the seed kernels of *Rhus succedanea* obtained from Fukkuoka, Japan, and also from the heartwood of *Garcinia multiflora* collected in Taiwan.

Amentoflavone (1),[53] agathisflavone (2),[54] robustaflavone (3),[55] hinokiflavone (4),[55] rhusflavanone (9)[37] and succedaneaflavanone (11)[28] were isolated from *Rhus succedanea.* Rhusflavanone hexaacetate (10) and succedaneaflavanone hexaacetate (12) were prepared directly from compounds (9) and (11), respectively.[37,38] Volkensiflavone (5), morelloflavone (7), GB-1a (13), GB-1a glucoside (15), and GB-2a (16) were isolated from *Garcinia multiflora.*[39,40] Volkensiflavone hexamethylether (6), morelloflavone hexamethylether (8), and GB-1a hexamethylether (14) were prepared from compounds (5), (7), and (13), respectively.[39,40] Robustaflavone tetrasulfate potassium salt (17) was prepared from robustaflavone (3).

In this example, two procedures for isolating robustaflavone are described. In the first procedure, robustaflavone was isolated by a dry-column method using benzene/pyridine/formic acid (20:5:1) as developing solvent, following an earlier reported procedure.[25] In order to eliminate the use of benzene and large quantities of pyridine, an improved procedure was developed wherein benzene and pyridine are replaced with other solvents. The solvent mixture of toluene/ethanol/formic acid in the ratio of 20:5:1 was used as the developing solvent in the dry-column procedure. Hinokiflavone was eluted completely from the dry-column and robustaflavone retained in the column. A mixture of ethanol and pyridine in the ratio of 4:1 was then used to elute robustaflavone from the column.

Extraction of Biflavanoids from *Rhus succedanea.*

The seeds (16 kg) of *Rhus succedanea* obtained from Fukuoka, Japan were coarsely powdered and defatted with benzene. The defatted seeds were exhaustibly extracted with boiling 95% EtOH (150 L). The combined EtOH extracts were concentrated in vacuo. The yellow pigments obtained during the concentration were filtered to yield crude pigment A (yield 0.2%) and pigment B (yield 0.2%), successively. Further concentration yielded yellow pigment C (ca. 2%).

Isolation of Robustaflavone from Pigment A

One gram of pigment A dissolved in 10 mL of pyridine was mixed with 5 g of silica gel (Kiselgel nach Stahl Type 60 Merck) and evaporated in vacuo to remove pyridine. The dried yellow powder obtained was packed on the top of a silica gel column ($SiO_2$ 100 g, 4×20 cm). The solvent mixture (400 mL) of benzene/pyridine/formic acid (40:10:2) was passed through the column. The column was sliced into seven bands (bands 1–7 from top to bottom). Extraction of the yellow band 4 with EtOAc and subsequent concentration of the extract yielded yellow crystals (200 mg), robustaflavone, which were recrystallized from pyridine-water, m.p. 350–352° C. (dec.). Mg—HCl test (orange red color), $FeCl_3$/EtOH test (brown color). IR $cm^{-1}$ (KBr): 3300 (OH), 1655, 1645 (CO), 1610, 1570, 1510, 1505, 1485 (aromatic ring), UV $\lambda_{max}$ (MeOH) nm (log $\epsilon$): 255 (4.71), 275 (4.44), 300 (4.42), 347 (4.49), $\lambda_{max}$ (NaOAc—MeOH) nm (log $\epsilon$): 257 (4.66), 277 (4.48), 313 (sh, 4.41), 378 (4.38), $\lambda_{max}$ ($AlCl_3$—MeOH) nm (log $\epsilon$) : 254 (4.80) , 278 (4.45), 300 (4.45), 342 (4.50), 388 (4.43); NMR (DMSO-$d_6$) (60 MHz) $\delta_{ppm}$: 7.87 (1H, d, J=2 Hz, H-2'), 7.94 (1H, dd, J=2 Hz, 9 Hz, H-6'), 7.09 (1H, d, J=9 Hz, H-5'), 7.97 (2H, d, J=9 Hz, H-2''', 6'''), 7.03 (2H, d, J=9 Hz, H-3''', 5'''), 6.23 (1H, d, J=2 Hz, H-6), 6.52 (1H, d, J=2 Hz, H-8), 6.68 (1H, s, H=8''), 6.80 (1H, s, H-3 or H3''), 6.83 (lH, s, H-3, or 3''), 13.53 (1H, s, HO-5), 13.28 (1H, s, HO-5''), 11.23–8.63 (4H, br., 4×OH), Anal, Calcd. for $C_{30}H_{18}O_{10} \cdot H_2O$: C, 64.75; H, 3.62, Found: C, 64.51; H, 3.83.

Improved Procedure for Isolating Robustaflavone

Pigment A (10 g) was dissolved in 50 mL of pyridine. The solution was added to 25 g of silica gel and thoroughly mixed. The pyridine was removed under reduced pressure using a rotary evaporator and the dry mixture ground to a fine particle size. To a 600 mL fritted filter funnel, incorporating a coarse porosity sinter with a disc of filter paper placed over the sinter, was added 250 g of silica gel. The absorbed Pigment A was then carefully placed and spread on the top of the silica gel in the funnel. The solvent system of toluene/ethanol/formic acid (40:10:2) (2.5 L) was passed through the funnel to remove the hinokiflavone. The eluent was collected and concentrated to provide 2.01 g of a yellow solid which was identified as hinokiflavone and a trace of robustaflavone.

The silica gel in the fritted funnel was allowed to dry out overnight. The top layer containing the absorbed Pigment A was then scrapped off the remaining silica gel and placed into a fritted filter funnel of coarse porosity containing a disc of filter paper. The silica gel containing the absorbed pigment A was then eluted using a mixture of toluene/ethanol/formic acid (40:10:2) (2.5 L), and then ethanol/pyridine (4:1) (4.5 L). The first eluting solution was concentrated to afford 1.1 g of a yellow solid which was identified as a mixture of robustaflavone and hinokiflavone, the major component being robustaflavone. The second eluting solution (ethanol/pyridine 4:1) was concentrated to afford robustaflavone (5.65 g). TLC, NMR, MS, and elemental analysis support these findings. NMR (H—NMR, $^{13}$C—NMR, COSY and HETCOR NMR: see Table 1).

Characterization of Robustaflavone

Robustaflavone was recrystallized from pyridine/water, mp. 350–352° C. (dec.). The compound gave an orange-red color in the Mg—HCl test and a brown color with alcoholic $FeCl_3$. The IR spectrum showed a broad hydroxyl absorption at 3250 $cm^{-1}$ and a conjugated carbonyl adsorption at 1650 $cm^{-1}$. The UV spectrum in MeOH exhibited four maxima in the region of 347 (log $\epsilon$ 4.38), 300 (4.42), 275 (4.44) and 255 (4.71) nm, and underwent a bathochromic shift on addition of NaOAc or $AlCl_3$. The UV spectrum in $AlCl_3$—MeOH was similar to that of in $AlCl_3$—MeOH upon addition of HCl, indicating the presence of OH groups at the 5,7 and 4' positions, and the absence of an o-dihydroxyl group.

The NMR spectrum (60 $MH_2$) of robustaflavone exhibited six OH groups at $\delta$ 13.53 (s, 1H), 13.28 (s, 1H) and 11.23–8.63 (br, 4H); the four protons in the 1,4-disubstituted benzene ring appeared at $\delta$7.97 (d, J=9 Hz, 2H) and 7.03 (d, J=9 Hz, 2H); the three protons in the 1,3,4-trisubstituted benzene ring appeared at $\delta$7.87 (d, J=9 Hz, 1H), 7.94 (dd, J=2 Hz, 9 Hz, 1H) and 7.09 (d, J=9 Hz, 1H); two aromatic protons appeared as meta-coupled doublets (J=2 Hz) at 6.23 (1H) and 6.52 (1H); three isolated protons appeared at $\delta$ 6.83(s), 6.80(s) and 6.68(s) respectively. The above evidence suggested that the structure of the compound was composed of two apigenin units joined by an interflavonyl linkage of C3'–C6, i.e. robustaflavone, an isomer of amentoflavone. This was further supported by examination of its acetate and methyl ether. Acetylation with pyridine/$Ac_2O$ yielded robustaflavone hexaacetate (3a) as colorless needles, m.p. 199–200° C. Methylation with $Me_2SO_4/K_2CO_3$ in dry acetone afforded a colorless compound, robustaflavone hexamethylether (3b), m.p. 300–305° C., $C_{36}H_{30}$ $O_{10}$, $M^+$ m/z 622. The induced change in the chemical shifts (ppm) owing to the addition of Eu(fod)$_3$ on compound (3b) represented by an S-value.[35] The S-values of MeO-II-5 and MeO-I-5 were 10.85 ppm (largest) and 2.17 ppm respectively, whereas H-I-8 was 0.34 ppm, indicating the presence of a linkage of CII-3'-CI-6 as structure (3b) which was characterized as hexa-O-methylrobustaflavone by comparison with an authentic sample (TLC, IR, NMR and MS).[35]

Although the isolation of minor amounts of hexa-O-methyl robustaflavone had been reported just at the time we isolated robustaflavone, the isolation of large quantities of robustaflavone has not yet been accomplished.

TABLE 1

Assignment of $^{13}$C—$^{1}$H HETCOR NMR

| | $^{13}$C-$\delta_{ppm}$ | | H-$\delta_{ppm}$ |
|---|---|---|---|
| I-2 | 164.11$^a$ | >C= | |
| II-2 | 163.86$^a$ | >C= | |
| I-3 | 102.86 | =CH | 6.81 (s) |
| II-3 | 116.10 | =CH | 6.84 (s) |
| I-4 | 181.74$^b$ | >CO | |
| II-4 | 181.83$^b$ | >CO | |
| I-5 | 161.20$^c$ | =C—OH | 13.02 (s) |
| II-5 | 159.61$^c$ | =C—OH | 13.23 (s) |
| I-6 | 108.89 | =C< | |
| II-6 | 98.82 | =CH | 6.20 (d, J=2.0 Hz) |
| I-7 | 162.06$^d$ | =C—OH | 10.82–10.00 (br) |
| II-7 | 163.65$^d$ | =C—OH | 10.82–10.00 (br) |
| I-8 | 93.44 | >CH | 6.65 (s, 1H) |
| II-8 | 94.05 | >CH | 6.49 (d, J=2.0 Hz) |
| I-9 | 161.46 | =C—O— | |
| II-9 | 157.5 | =C—O— | |
| I-10 | 103.57 | =C< | |
| II-10 | 103.72 | =C< | |

TABLE 1-continued

Assignment of $^{13}$C—$^1$H HETCOR NMR

| | $^{13}$C-δ$_{ppm}$ | | H-δ$_{ppm}$ |
|---|---|---|---|
| I-1' | 121.22 | =C< | |
| II-1' | 120.89 | =C< | |
| I-2' | 128.55 | =CH | 7.99 (d, J=8.8 Hz) |
| II-2' | 130.87 | =CH | 7.79 (d, J=2.2 Hz) |
| I-3' | 116.01 | =CH | 6.96 (d, J=8.8 Hz) |
| II-3' | 120.86 | =C< | |
| I-4' | 156.35 | =C—OH | 10.40 (br) |
| II-4' | 159.07 | =C—OH | 10.20 (br) |
| I-5' | 116.01 | =CH | 6.96 (d, J=8.8 Hz) |
| II-5' | 102.86 | =CH | 7.05 (d, J=8.7 Hz) |
| I-6' | 128.55 | =CH | 7.99 (d, J=8.88 Hz) |
| II-6' | 127.57 | =CH | 7.93 (dd, J=8.7 & 2.2 Hz) |

Assignments bearing the same alphabetical superscript in the spectrum may be reversed.

The high resolution CI mass spectrum provided an M+H ion, m/z 539.096993, $C_{30}H_{19}O_{10}$, which requires 539.097821572. The infrared spectrum exhibited a broad hydroxyl absorption at 3250 cm$^{-1}$ and a conjugated carbonyl absorption at 1650 cm$^{-1}$. The UV spectrum in MeOH contained four maxima in the region of 345 (log ε 4.49), 300 (4.42), 275 (4.44) and 255 (4.71 nm, and underwent a bathochromic shift on addition of NaOAc or AlCl$_3$. The UV spectrum in AlCl$_3$—MeOH was similar to that obtained in AlCl$_3$—MeOH on addition of HCl, indicating the presence of OH groups in the 5,7 and 4' positions, and the absence of an o-dihydroxy group.[26] [$\lambda^{NaOAc—MeOH}$ (log ε) 378 (4.38), 313 (sh 4.41), 277 (4.48), 257(4.66) nm; $\lambda^{AlCl3—MeOH}$ (log ε) 388 (4.43), 352 (4.50), 300 (4.45), 278 (4.45), 254 (4.80 nm).

The NMR (300 MHz) spectrum of robustaflavone contained six OH groups at δ 13.25 (1H, s), 13.02 (1H, s), 10.83 (1H, s), 10.40 (1H, s), 10.4–10.9 (2H, br.); the four protons in the 1,4-disubstituted benzene ring at δ 7.98 (2H, d, J=8.88 Hz, H-2''', 6''') and 6.96 (2H, d, J=8.88 Hz, H-3''', 5'''); the three protons in the 1,3,4-trisubstituted benzene ring at δ 7.93 (1H, dd., J=8.7 Hz and 2.2 Hz, H-6'), 7.79 (1H, d. J=2.2 Hz, H-2') and 7.05 (lH, d, J=8.7 Hz, H-5'); the five aromatic protons at δ 6.84 (1H, s, H-3'), 6.8 (1H, s, H-3"), 6.65 (1H, s, H-8"), 6.49 (1H, d, J=2.0 Hz, H-8) and 6.20 (1H, d, J=2 Hz, H-6).

EXAMPLE 2

General Procedure for Synthesizing O-Acyl Biflavanoids

Procedure 1: To a solution of biflavanoid in anhydrous dichloromethane containing 20% dry pyridine is added an appropriate acyl chloride or anhydride at 0° C. or at room temperature. The mixture is allowed to stand overnight, and the volatiles are evaporated in vacuo. Alternatively, the mixture is poured into water and extracted with chloroform. The organic layer is washed with water and brine, dried over anhydrous sodium sulfate, and concentrated in vacuo. The residue is chromatographed on preparative TLC or a silica gel column to afford the product.[78]

Procedure 2: Preparation of acetate: Biflavanoid is reacted with acetic anhydride in pyridine at room temperature overnight. The reaction mixture is poured into ice water. The precipitate is filtered and washed with cold 1% hydrochloric acid and then with water to give biflavanoid acetate.[37]

Rhusflavanone hexaacetate: Acetylation of rhusflavanone (200 mg) with Ac$_2$O/Pyridine at room temperature for 20 h gave hexaacetate (110 mg) as micro needles, m.p. 130–131° C., EIMS M$^+$ m/z 794; IR cm$^{-1}$ (KBr) 1770 (acetoxy CO), 1688 (flavanone CO), 1603, 1560, 1510 and 1490 (arom.); H—NMR δ (CDCl$_3$): 2.02 (3H, s, AcO-7"), 2.10 (3H, s, AcO-7), 2.15 (3H, s, AcO-5), 2.28 (3H, s, AcO-4"'), 2.32 (3H, s, AcO-4'), 2.40 (3H, s, AcO-5"), 2.85–3.06 (4H, m, H-3.3"), 5.45–5.35 (2H, m, H-2, 2"), 6.71 (1H, s, H-6"), 6.91 (1H, s, H-8), 7.14 (2H, d, J=9 Hz, H-3''', 5'''), 7.17 (2H, d, J=9 Hz, H-3', 5'), 7.44 (2H, d, J=9 Hz, H-2''', 6'''), 7.55 (2H, d, J=9 Hz, H-2', 6').

Succedaneaflavanone hexaacetate: Acetylation of suc-cedaneaflavanone by Procedure No. 2 produced succedaneaflavanone hexaacetate as white needles. m.p. 252–255° C. (from CHCl$_3$—MeOH), IR cm$^{-1}$ (KBr): 1770 (OAc), 1688 (flavanone CO), 1613, 1560, 1510 (arom.); H—NMR δ (CDCl$_3$): 2.10 (6H, s, AcO-7, 7"), 2.17 (6H, s, AcO-5,5"), 2.33 (6H, s, AcO-4', 4'''), 2.83–3.27, 4H, m, H-3, 3"), 5.63 (2H, dd, J=12 Hz, 4 Hz, H-2, 2"), 6.97 (2H, s, H-8, 8"), 7.25 (4H, d, J=8 Hz, H-3', 5', 3", 5"), 7.58 (4H, d, J=8 Hz, H-2', 6', 2''', 6''').

EXAMPLE 3

General Procedure for Synthesizing Biflavanoid Ethers

Preparation of biflavanoid alkyl ethers: To a mixture of biflavanoid and Ag$_2$O (catalytic amount) in DMF is added a corresponding alkyl halide at 10–12° C. After stirring for 2.5–4 h, the reaction mixture is kept in a refrigerator overnight. The catalyst is filtered, and the filtrate is washed with water and brine and then concentrated in vacuo. The resiude is purified by column chromatography on silica gel to yield the product.[78]

Preparation of biflavanoid methvl ethers: Biflavanoid is dissolved in anhydrous acetone and potassium carbonate and dimethyl sulfate are added. The solution is refluxed for 4 h. The precipitate (potassium carbonate) is filtered and the filtrate is concentrated under vacuum. The residue is dissolved in chloroform and washed with brine, dried with magnesium sulfate and concentrated under vacuum. The resulting crude product is purified by silica gel column chromatography or preparative thin layer chromatography and then recrystallized with ethyl acetate, ethanol, or chloroform to afford biflavanoid methyl ethers.[37]

Volkensiflavone Hexamethyl Ether (6)

Volkensiflavanone (200 mg) was dissolved in 30 mL of anhydrous acetone, and 4 g of potassium carbonate and 3 mL of dimethyl sulfate were added. The solution was refluxed for 4 h. The precipitate (potassium carbonate) was filtered and the filtrate was concentrated under vacuum. The reddish brown oily residue was dissolved in 15 mL of chloroform and the chloroform solution was washed with brine twice and then water. The chloroform layer was dried with magnesium sulfate and concentrated under vacuum. The residue was purified by silica gel column chromatography and eluted with the mixture of toluene and ethyl acetate in the ratio of 1:1. The eluent was concentrated under vacuum and the residue was recrystallized with methanol/chloroform to obtain 135 mg of white crystals, m.p. 258–260° C., EIMS M$^+$ m/z 624; IR cm$^{-1}$ (KBr): 2900, 2950, 2850 (OMe), 1680 (flavanone CO), 1645 (flavone CO), 1600, 1580, 1510 and 1490 (arom.) H—NMR δ (CDCl$_3$): 3.93 (3H, s, OMe), 3.87 (3H, s, OMe); 3.83 (6H, s, OMe), 3.77 (3H, s, OMe), 3.67 (3H, s, OMe), 4.90 (lH, d, J=12 Hz, H-3), 5.8 (1H, d, J=12 Hz, H-2), 6.22 (1H, d, J=2 Hz, H-6), 6.23 (1H, s, H-6'''), 6.32

(1H, d, J=2 Hz, H-8), 6.50 (1H, s, H-3"), 6.63 (1H, s, J=9 Hz, H-3', 5'), 6.87 (2H, d, J=9 Hz, H-3''', 5'''), 7.13 (2H, d, J=9 Hz, H-2', 6'), 7.70 (2H, d, J=9 Hz, H-2''', 6'').

GB-1a Hexamethyl Ether (14)

GB-1a (200 mg) was methylated by the method described above. The resulting crude methyl ether was purified by preparative thin layer chromatography using ethyl acetate as developing solvent. The band at Rf 0.35 was scraped off and extracted with ethyl acetate. The ethyl acetate extract was concentrated under vacuum and the residue was recrystallized from the solvent mixture of acetone and hexane (1:1) to afford a white solid, 118 mg, m.p. 132–134° C., EIMS M$^+$ m/z 626, IR cm$^{-1}$ (KBr), 2990, 2930, 2900, 2830 (OMe); 1675 (flavanone CO), 1600, 1570 and 1515 cm$^{-1}$ (arom.); H—NMR δ (CDCl$_3$): 2.72 (2H, m, H-3"), 3.90 (6H, s, 2×OMe), 3.83 (6H, s, 2×OMe), 3.90 (6H, s, 2×OMe), 4.70 (1H, d, J=12 Hz, 3-H), 5.28 (1H, m, H-2"), 5.73 (1H, d, J=12 Hz, H-2), 6.08 (1H, d J=2 Hz, H-6), 6.15 (1H, s, H-6"), 6.17 (1H, d, J=2 Hz, H-8), 6.82 (2H, d, J=8 Hz, H-3', 5'), 6.90 (2H, d, J=8 Hz, H-3''', 5'''), 7.28 (2H, d, J=8 Hz, H-2', 6'), 7.32 (2H, d, J=8 Hz, H-2''', 6''').

EXAMPLE 4

General Procedure for Preparation of Biflavanoid Sulfates

The dicyclohexylcarbodiimide (DDC)-mediated esterification of flavones and flavonols with tetrabutylammonium hydrogen sulfate (TBSHS) resulted in the formation of mono-, di-, and trisulfated products by controlling the reaction temperature and amount of reagents. Sulfation occurred mainly at positions 7,4' and 3 of the flavonoid skeleton and followed the order 7>4'>3.[80]

Biflavanoid partial sulfate esters are prepared by treating the biflavanoid with TBAHS (tetrabutylammonium hydrogen sulfate) and DDC (dicyclohexylcarbodiimide) in pyridine using controlled amounts of reagents and temperature. The reaction product, sulfate ester TBA-salt, is separated from minor by-products by gel filtration. The sulfate ester TBA-salt is converted to the potassium salt by treatment with saturated methanolic potassium carbonate. The resulting potassium salt is purified by repeated chromatography on Sephadex G-10 column using a 0–50% gradient of aqueous methanol.[80]

Robustaflavone Tetrasulfate K-salt

A solution of robustaflavone (46.1 mg, 0.086 mM, 1.0 equivalent) in pyridine (5 mL) was treated with 1,3-dicyclohexylcarbodiimide (DCC) (500 mg, 2.423 mM, 28.17 equivalent) and tetrabutylammonium hydrogen sulfate (TBAHS) (97.5 mg, 0.287 mM, 3.34 equivalent) at 4° C. (in refrigerator) for 86 hours. The reaction solution was diluted with MeOH and the dicyclohexylurea precipitate was removed by filtration. The supernatant was chromatographed on Sephadex LH-20 (3 g, in MeOH) and eluted with MeOH and a MeOH-acetone (1:1) mixture. The yellow fractions containing robustaflavone tetrasulfate were concentrated to 5 mL and then treated with 15 mL of saturated K$_2$CO$_3$ in MeOH. The precipitate of robustaflavone tetrasulfate K-salt was collected by filtration and washed with MeOH (3 ml×9) and water 3 mL×5), successively. The MeOH and water washes were collected separately. The water solution was lyophilized to obtain 72 mg robustaflavone-7,4',7'',4'''-tetrasulfate K-salt as a yellow powder, $^1$H—NMR (DMSO, 300 MHz) δ 6.56 (1H, bs, H-6), 7.19 (1H, bs, H-8), 6.78 (1H, s, H-3), 7.75 (1H, dd, J=9.0, 2.0 Hz, H-6'), 7.87 (1H, d, J=9.0 Hz, H-5'), 8.31 (1H, d, J=2.0 Hz, H-2'), 6.85 (1H, s, H-8), 6.75 (1H, s, H-3"), 7.33 (2H, d, J=9.0 Hz, H-3''', 5'''), 7.94 (2H, d, J=9.0 Hz, H-2''', 6''').

EXAMPLE 5

General Procedure for Preparation of Biflavanoid Acid Salt

The dried mixture of biflavanoid, appropriate acid anhydride, and appropriate catalyst, such as 4-dimethylaminopyridine are dissolved in dry pyridine. The solution is worked-up by standard methods to yield biflavanoid acid adduct. The biflavanoid acid can be converted to the potassium salt by treatment with saturated methanolic potassium carbonate.[79]

EXAMPLE 6

Antiviral HBV Activity of Biflavanoids

In this example, robustaflavone and related biflavanoids were screened for hepatitis B (HBV) antiviral and cytotoxicity activity.

Antiviral HBV Assay. The inhibition of HBV replication in cultures of 2.2.15 cells was assayed using chronically HBV-producing human liver cells which were seeded into 24-well tissue culture plates and grown to confluence. Test compounds were added daily for a nine continuous day period; the culture medium was collected and stored for analysis of extracellular (virion) HBV DNA after 0, 3, 6, and 9 days of treatment. The treated cells were lysed for 24 hours following day 9 of treatment for the analysis of intracellular HBV genomic forms. The overall levels of HBV DNA (both extracellular and intracellular DNA) and the relative rate of HBV replication (intracellular DNA) were analyzed quantitatively. The analysis was performed using blot hybridization techniques and [$^{32}$P]-labeled HBV-specific probes. The HBV DNA levels were measured by comparison to known amounts of HBV DNA standards applied to every nitrocellulose membrane (gel or slot blot). An AMBIS beta scanner, which measures the radioactive decay of the hybridized probes directly from the nitrocellulose membranes, was used for the quantitative analysis. Standard curves, generated by multiple analyses, were used to correlate CPM measurements made by the beta scanner with relative levels of target HBV DNA. The levels of HBV virion DNA released into the culture medium were analyzed by a slot blot hybridization procedure. HBV DNA levels were then compared to those at day 0 to determine the effect of the test compound. A known positive drug was evaluated in parallel with test compounds in each test. This drug was 2',3'-dideoxycytosine (2',3'-ddC). The data were expressed as 50% effective (virus-inhibitory) concentrations (EC$_{50}$). The 90% effective concentration (EC$_{90}$), which is that test drug concentration that inhibits virus yield by 1 log$_{10}$, was determined from these data. Each test compound's antiviral activity was expressed as a selectivity index (SI), which is the CC$_{50}$ or CC$_{90}$, the concentration of compound which killed 50% or 90% of the treated cells, divided by the EC$_{50}$. Generally an SI of 10 or greater is indicative of positive antiviral activity, although other factors, such as a low SI for the positive control, are also taken into consideration.

HBV Cytotoxicity Assays. The toxicity of the test compounds in cultures of 2.2.15 cells, grown to confluence in 96-well flat-bottomed tissue culture plates and treated with compounds as described above, were assayed at four concentrations each in triplicate cultures, in 3 to 10-fold steps. Untreated control cultures were maintained on each plate. On each plate, wells containing no cells were used to correct for light scattering. The toxicity was determined by the inhibition of the uptake of neutral red dye, determined by absorbance at 510 nm relative to untreated cells, 24 hours following day 9 of treatment.

Analysis of HBV Nucleic Acids and Proteins. HBV viron DNA in culture medium, and intracellular HBV RI and HBV RNA levels were determined by quantitative blot hydridization analyses (dot, Southern, and Northern blot, respectively)[81,82] Nucleic acids were prepared by previously described procedures. Integrated HBV DNA, which remains at a stable level per cell during the treatment period, was used to quantitate the amount of cellular DNA transferred in each Southern gel lane.[81,82] For the HBV RNA analyses, the levels of β-actin RNA were used to quantitate the amount of cellular RNA transferred in each Northern gel lane. Previous examinations of β-actin-specific RNA in confluent cultures of 2.2.15 cells demonstrated a steady state level of approximately 1.0 pg β-actin RNA/μg unfractionated cellular RNA.[81] $EC_{90}$ values (10-fold depression of HBV DNA levels relative to untreated (control) cultures were determined by linear regression.[82] $EC_{90}$ values were used for comparison since, in this culture system, DNA levels within 3-fold of control values are not generally statistically significant.[83]

Values of HBV proteins were determined by semi-quantitative EIA performed as previously described.[83] For the EIA analyses, test samples were diluted (2- to 10-fold) so that the assay values produced were within the linear dynamic range of the EIA assays. Standard curves using serial dilutions of positive assay controls were included in each set of EIA analyses. HBV surface antigen (HBcAg), preS1 protein, and HBc antigen (HBCAg) are released as extracellular products and were therefore analyzed in culture medium obtained 24 h following the last treatment dose of oligonucleotides or 2', 3'-ddc. HBV core antigen (HBcAg) is an intracellular viral protein and was assayed in cell extracts produced by Triton-X-100 lysis.[83]

Cultures for HBV RNA were maintained on 6-well plates, cultures for HBV virion DNA analyses were maintained on either 96- or 24-well plates, and cultures for all other HBV parameters were maintained on 24-well plates.

The concentrations of antiviral agents used in these studies approximates the $EC_{50}$ values of the individual agents against intracellular HBV DNA replication intermediates (HBV RI). Cultures were treated with the indicated agents for 9 days using standard procedures. Values reported are the levels of the indicated HBV markers at the end of the treatment period ("DAY 9") expressed as a percentage (±standard deviation (S.D.)) of the average levels in the control cultures at the beginning of the treatment period ("DAY 0"). The method of expression permits an analysis of the variation of the HBV markers in the untreated (control) cultures over the course of the treatment period. HBV nucleic acid levels were measured by standard blot hydridization (dot, Southern, or Northern). HBV protein levels were measured by standard semi-quantitative EIA methods. Cultures for HBV RNA were maintained in 6-well culture plates. The levels of each of two major classes of HBV RNA transcripts are listed separately. The 2.1 kb transcript is believed to encode for HBaAg. Cultures for all other HBV markers were maintained in 24-well culture plates. For each treatment, a total of 4 separate cultures were used for the analysis of each HBV marker at both DAY 0 and DAY 9.

Results. Tables 2 and 3 present evidence that robustaflavone is an extremely effective anti-HBV agent against the hepatitis B virus in comparison to the control drug, 2',3'-ddC. It was observed from the results that robustaflavone exhibited an impressive in vitro activity against extracellular (virion) HBV DNA, with an effective average concentration ($EC_{50}$) of 0.25 μM and an average selectivity index ($CC_{50}/EC_{90}$) of 153; compared to an effective average $EC_{50}$ of 1.4 μM and average SI of 31 for 2',3'-ddC. Furthermore, measurement of the relative rate of HBV replication intermediates (RI) (intracellular DNA) again indicates the effectiveness of robustaflavone over the control drug, 2',3'-ddC. Robustaflavone exhibits an effective $EC_{50}$ of 0.6 μM and SI of 80; compared to an $EC_{50}$ of 2.4 μM and SI of 24 for 2',3'-ddC. Volkensiflavone hexamethyl ether (6), rhusflavanone acetate (10) and succendaneaflavanone hexaacetate (12) exhibited moderate anti-HBV activity while amentoflavone (1), agathistflavone, hinokiflavone (4), volkensiflavone (5), rhusflavanone (9) and succendaneaflavanone possessed little or no anti-HBV activity.

In summary, measurement of the overall levels of HBV DNA (both extracellular and intracellular DNA) and the relative rate of HBV replication intermediate (RI) (intracellular DNA) clearly demonstrates the effectiveness of robustaflavone against HBV.

TABLE 2

| | Hepatitis B Virus (HBV) HBV Virion | | |
|---|---|---|---|
| Sample | $EC_{50}$[1] μM | $EC_{90}$[2] μM | SI[3] ($CC_{50}/EC_{90}$) |
| 2',3'-ddC* | 1.8 | 9.4 | 28 |
| Amentoflavone (1) | >100 | >100 | ND |
| Agathisflavone (2) | >100 | >100 | ND |
| Robustaflavone (3) | 0.25 | 2.4 | 153 |
| Hinokiflavone (4) | >100 | >100 | ND |
| Volkensiflavone (5) | >100 | >100 | ND |
| Volkensiflavone hexamethyl ether (6) | 11 | 108 | 1.3 |
| Rhusflavanone (9) | >100 | >100 | ND |
| Rhusflavanone hexaacetate (10) | 7.1 | 6.2 | 2.8 |
| Succedaneaflavanone (11) | >100 | >100 | ND |
| Succedaneaflavanone hexaacetate (12) | 3.5 | 128 | 1.9 |
| Robustaflavone tetrasulfate (17) | 0.4 | 3.6 | 110 |

*Positive drug control;
*[1]50% effective dose;
*[2]90% effective dose ($EC_{90}$);
*[3]selective index: $CC_{50}/EC_{50}$

TABLE 3

Effect of Antiviral Agents on HBV Proteins
and Nucleic Acids in 2.2.15 Cells
Relative Levels of HBV Proteins and Nucleic Acids
(Day 9, % of Day 0 Control ± SD)

| Treatment | Virion DNA | HBV RI | HBV RNA 3.6 kb | HBV RNA 2.1 kb | HBsAg | HBeAg | HbcAG |
|---|---|---|---|---|---|---|---|
| Untreated cells | 127 ± 8 | 103 ± 11 | 90 ± 12 | 101 ± 10 | 117 ± 11 | 108 ± 5 | 86 ± 10 |
| 2',3'-ddC @ 10 μM | 1 ± 1 | 6 ± 1 | 94 ± 7 | 87 ± 9 | 90 ± 12 | 88 ± 10 | 91 ± 9 |
| Robustaflavone @ 10 μM | 1 ± 1 | 5 ± 1 | 93 ± 10 | 106 ± 11 | 97 ± 6 | 86 ± 6 | 138 ± 8 |

EXAMPLE 7

Anti-Respiratory Viral Activity of Biflavanoids

In this example, robustaflavone and related biflavanoids were screened for respiratory (influenza A and B, RSV, parainfluenza 3, adenovirus 5, and measles) antiviral and cytotoxic activities.

Anti-Respiratory Viral Assay. The viruses used in the primary screen for antiviral activity against respiratory viruses consisted of: (1) Influenza A and B-Virus strains: A/Texas/36/91 (H1N1) (Source: Center for Disease Control (CDC), A/Beijing/2/92 (H3N2) (Source: CDC), B/Panama/45/90 (Source: CDC), A/NWS/33 (H1N1) (Source: American Type Culture Collection [ATCC]). (All but A/NWS/33 are tested in the presence of trypsin.); cell lines: Madin Darby canine kidney (MDCK) cells; (2) Respiratory syncytial virus—Virus strain: Utah 89 (Source: Utah State Diagnostic Laboratory, cell line: African green monkey kidney (MA-104) cells; (3) Parainfluenza type 3 virus—Virus strain: C243 (Source: ATCC); cell line: African green monkey kidney (MA-104) cells; (4) Measles virus—Virus strain: CC (Source: Pennsylvania State University; cell line: African green monkey kidney (BSC-1) cells; and (5) Adenovirus type 5—Virus strain: Adenoid 75 (Source: ATCC); cell line: Human lung carcinoma (A549) cells.

Test compounds were assayed for continual activity and cytotoxicity. Three methods were used for assay of antiviral activity: (1) inhibition of the viral cytopathic effect (CPE); (2) increase in the neutral red (NR) dye uptake; and (3) decrease in the virus yield. Methods for ascertaining cytotoxicity were visual observation, neutral red uptake, and viable cell count.[32]

Inhibition of the Viral Cytopathic Effect (CPE). The test for CPE was run in 96-well flat-bottomed microplates and was used for the initial antiviral evaluation of all new test compounds. In this CPE inhibition test, seven one-half $\log_{10}$ dilutions of each test compound were added to 4 cups containing the cell monolayer; within 5 min, the virus was then added and the plate sealed, incubated at 37° C. and CPE read microscopically when untreated infected controls develop a 3 to 4+ CPE (approximately 72 h). A known positive drug was evaluated in parallel with test drugs in each test. This drug was ribavirin for influenza, measles, respiratory syncytial, and parainfluenza viruses, and (S)-1-(3-hydroxy-2-phosophonylmethoxypropyl)adenine (HPMPA) for adenovirus. The data were expressed as 50% effective (virus-inhibitory) concentrations ($EC_{50}$).

Increase in the Neutral Red (NR) Dye Uptake. The test for increase in the NR dye uptake was run to validate the CPE inhibition seen in the initial test, and utilizes the same 96-well microplates after the CPE has been read. Neutral red dye was added to the medium; cells not damaged by virus take up a greater amount of dye, which was read on a computerized microplate autoreader. An $EC_{50}$ value was determined from this dye uptake.

Decrease in virus yield. Compounds considered active by CPE inhibition and NR uptake were retested using both CPE inhibition, and, using the same plate, the effect on reduction of virus yield was determined by assaying frozen and thawed eluates from each cup for virus titer by serial dilution onto monolayers of susceptible cells. Development of CPE in these cells was an indication of presence of infectious virus. As in the initial tests, a known active drug (ribavirin) was run in parallel as a positive control. The 90% effective concentration ($EC_{90}$), which was that test drug concentration that inhibits virus yield by 1 $\log_{10}$, was determined from these data.

Cytotoxicity Assays. These assays consist of visual observation, neutral red dye uptake, and viable cell count.

Visual Observation—In the CPE inhibition tests, two wells of uninfected cells treated with each concentration of test compound were run in parallel with the infected, treated wells. At the same time CPE was determined microscopically, the toxicity control cells were examined microscopically for any changes in cell appearance compared to normal control cells run in the same plate. These changes were given a designation conforming to the degree of cytotoxicity seen (e.g., enlargement, granularity, cells with ragged edges, a cloudy appearance, rounding, detachment from the surface of the well, or other changes. These changes were given a designation of T (100% toxic), Pvh (partially toxic-very heavy 80%), Ph (partially toxic-heavy 60%), P (partially toxic-40%), Psi (partially toxic-slight- 20%), or 0 (no toxicity –0%), conforming to the degree of cytotoxicity seen. A 50% cell inhibitory (cytotoxic) concentration ($IC_{50}$) was determined by regression analysis of the data.

Neutral Red Dye Uptake—In the neutral red dye uptake phase of the antiviral test described above, the two toxicity control wells also receive neutral red dye and the degree of color intensity was determined spectrophotometrically. A neutral red $IC_{50}$ was subsequently determined.

Viable Cell Count—Compounds considered to have significant antiviral activity in the initial CPE and NR tests were retested for their effects on cell growth. In this test, 12-well tissue culture plates were seeded with cells (sufficient to be approximately 20% confluent in the well) and exposed to varying concentrations of the test drug while the cells were dividing rapidly. The plates were then incubated in a $CO_2$ incubator at 37° C. for 72 h, at which time the media-drug solution was removed and the cells washed. Trypsin was added to remove the cells, which were then counted using a Coulter cell counter. An $IC_{50}$ was then determined using the average of three separate counts at each drug dilution.

Each test compound's antiviral activity was expressed as a selectivity index (SI), which was the $IC_{50}$ or $IC_{90}$ divided by $EC_{50}$. Generally an SI of 10 or greater was indicative of positive antiviral activity, although other factors, such as a low SI for the positive control, were also taken into consideration.

Anti-Influenza A and Anti-Influenza B Activity

Compounds 1–6 and 9–12 have been screened for inhibitory activity against influenza A (strains H1N1 and H3N2) and influenza B viruses. For these compounds both cytopathic effect inhibition (CPE) and neutral red uptake test methods were investigated. The results are displayed on Tables 4–6. For the results shown in Tables 4–6 the selective index (SI) is calculated as $IC_{50}$ (50% cell inhibitor (cytotoxic) concentration) over the $EC_{50}$ (50% effective concentration).

Influenza A. Tables 4 and 5 provide data that robustaflavone (3) had significant antiviral activity towards two influenza A strains, when compared to the control drug, ribavirin. The effective concentrations ($EC_{50}$) of robustaflavone (3) were 1.9 μg/mL for both influenza A H1N1 (Table 4) and H3N2 (Table 5) strains, as compared to 1.9 and 4.1 μg/mL for the control drug, ribavirin. The $IC_{50}$ values for robustaflavone were 18 and 32 μg/mL, respectively for H1N1 and H3N2 in the CPE assay. However, the selectivity indexes (SI) for ribavirin were 296 and 137 against influenza A strains H1N1 and H3N2, respectively, as compared to 9.5 and 17 for robustaflavone (3). The effective neutral red concentrations ($EC_{50}$) of robustaflavone (3) were 2.0 and 1.8 μg/mL for influenza A strains H1N1 and H3N2, respectively and the $IC_{50}$ values were ~32 and ~100 pg/mL. This compared favorably with ribavirin, which had effective neutral red concentrations of 1.4 and 5.7 μg/mL, respectively for these strains. The SI's for neutral red uptake for ribavirin were 132 and 70, respectively, toward influenza A strains H1N1 and H3N2, whereas those for robustaflavone (3) were 16 and 56.

Amentoflavone (1) also demonstrated significant antiviral activity against both strains of influenza A. The $EC_{50}$ values of amentoflavone (1) were 3.1 and 4.3 μg/mL, respectively in CPE inhibition tests. The $IC_{50}$ values were 22 and >100 μg/mL, therefore it had SI values of 7.1 and >23 for influenza A strains H1N1 and H3N2. The other biflavanoids assayed were either inactive or toxic, except for agathisflavone which produced an SI value of >18 for the neutral red assay, but only 1 for the CPE assay. The acetylation of rhusflavanone (9), to rhusflavanone hexaacetate (10), slightly increased both the activity and toxicity against both influenza A strains in both assays. The acetylation of succedaneaflavanone (11) did not change the activity or toxicity considerably, and methylation of volkensiflavone (5) to volkensiflavone hexamethyl ether (6) resulted in a decrease in both the activity and the toxicity, in both the CPE inhibition and the neutral red assays. As shown in Tables 4 and 5, the modifications to these three compounds did result in changes in activity and toxicity, but none produced significant changes in the SI value.

TABLE 4

| | Influenza A (H1N1) Virus: Texas /36/91 | | | | | |
|---|---|---|---|---|---|---|
| | CPE Inhibition | | | Neutral Red | | |
| Sample | $EC_{50}^{*1}$ μg/mL | $IC_{50}^{*2}$ μg/mL | $SI^{*3}$ | $EC_{50}^{*1}$ μg/mL | $IC_{50}^{*2}$ μg/mL | $SI^{*3}$ |
| Ribavirin* | 1.9 | 562 | 296 | 1.4 | 185 | 132 |
| Amentoflavone (1) | 3.1 | 22 | 7.1 | 5.3 | >100 | 19 |
| Agathisflavone (2) | 6.6 | 6.5 | 1.0 | 5.6 | >100 | 18 |
| Robustaflavone (3) | 1.9 | 18 | 9.5 | 2.0 | 32 | 16 |
| Hinokiflavone (4) | >1.0 | 1.4 | <1.4 | 1.8 | 2.0 | 1.1 |
| Volkensiflavone (5) | >32 | 13 | 0 | 15 | 14 | 1.0 |
| Volkensiflavone hexamethyl ether (6) | ><100 | <24 | 0 | ><100 | ><100 | 0 |
| Rhusflavanone (9) | >10 | 8.2 | 0 | 24 | 26 | 1.1 |
| Rhusflavanone hexaacetate (10) | >10 | 7.2 | 0 | 5.6 | 5.7 | 1.0 |
| Succedaneaflavanone (11) | >3.2 | 4.9 | <1.5 | 5.2 | 5.0 | 1.0 |
| Succedaneaflavanone hexaacetate (12) | 5.6 | 8.2 | 1.5 | 7.4 | 7.4 | 1.0 |

*Positive control drug;
*1 50% effective dose;
*2 50% cell inhibitory (cytotoxic) concentration;
*3 selective index: $IC_{50}/EC_{50}$

TABLE 5

| | Influenza A (H3N2) Virus: Beijing /32/92 | | | | | |
|---|---|---|---|---|---|---|
| | CPE Inhibition | | | Neutral Red | | |
| Sample | $EC_{50}^{*1}$ μg/mL | $IC_{50}^{*2}$ μg/mL | $SI^{*3}$ | $EC_{50}^{*1}$ μg/mL | $IC_{50}^{*2}$ μg/mL | $SI^{*3}$ |
| Ribavirin* | 4.1 | 562 | 137 | 5.7 | 397 | 70 |
| Amentoflavone (1) | 4.3 | >100 | >23 | 6.5 | >100 | >15 |
| Agathisflavone (2) | 24 | 18 | 0.8 | 13 | 19 | 1.5 |
| Robustaflavone (3) | 1.9 | ><32 | 17 | 1.8 | ><100 | 56 |
| Hinokiflavone (4) | >3.2 | 1.3 | 0 | 1.9 | 2.2 | 1.2 |
| Volkensiflavone (5) | 56 | 42 | 0.8 | 38 | 37 | 1.0 |
| Volkensiflavone hexamethyl ether (6) | ><100 | ><100 | 0 | ><100 | ><100 | 0 |
| Rhusflavanone (9) | >32 | 24 | 0 | 31 | 31 | 1.0 |
| Rhusflavanone hexaacetate (10) | >10 | 5.6 | 0 | 5.4 | 5.3 | 1.0 |
| Succedaneaflavone (11) | >10 | 12 | <1.2 | 12 | 12 | 1.0 |
| Succedaneaflavone (12) | 8.8 | 12 | 1.4 | 5.6 | 5.6 | 1.0 |

*Positive control drug;
*1 50% effective dose;
*2 50% cell inhibitory (cytotoxic) concentration;
*3 selective index: $IC_{50}/EC_{50}$ Influenza B. Table 6 indicates that robustaflavone had significant antiviral activity towards influenza B, when compared to the control drug, ribavirin. The effective concentration ($EC_{50}$) of robustaflavone was an impressive 0.23

μg/mL, compared to 1.5 for ribavirin. The selectivity index (SI) for ribavirin was >667 against influenza B; as compared to <435 for robustaflavone. The effective neutral red concentration ($EC_{50}$) of robustaflavone was 0.22 μg/mL, compared to the control drug, ribavirin, 0.48 μg/mL. The SI for neutral red uptake for ribavirin was 208, compared to 454 for robustaflavone.

TABLE 6

| | Influenza B Virus: Panama /45/90 | | | | | |
|---|---|---|---|---|---|---|
| | CPE Inhibition | | | Neutral Red | | |
| Sample | $EC_{50}^{*1}$ μg/mL | $IC_{50}^{*2}$ μg/mL | $SI^{*3}$ | $EC_{50}^{*1}$ μg/mL | $IC_{50}^{*2}$ μg/mL | $SI^{*3}$ |
| Ribavirin* | 1.5 | >1000 | >667 | 0.48 | 100 | 208 |
| Amentoflavone (1) | 0.56 | 100 | 178 | — | — | — |
| Agathisflavone (2) | 3.2 | 18 | 5.6 | — | — | — |
| Robustaflavone (3) | 0.23 | ><100 | ><435 | 0.22 | ><100 | 454 |
| Hinokiflavone (4) | >1.0 | 1.2 | <1.2 | 1.9 | 2.0 | 1.0 |
| Volkensiflavone (5) | 1.1 | 38 | 34 | 4.5 | 20 | 4.4 |
| Volkensiflavone hexamethyl ether (6) | 2.6 | ><100 | ><38 | <20 | ><100 | 5.0 |
| Rhusflavanone (9) | 4.1 | 38 | 9.3 | — | — | — |
| Rhusflavanone hexaacetate (10) | >10 | 4.2 | 0 | — | — | — |
| Succedaneaflavanone (11) | 0.97 | 15 | 15 | 2.2 | 7.0 | 3.2 |
| Succedaneaflavanone hexaacetate (12) | 5.4 | 12 | 2.2 | 5.9 | 5.9 | 1.0 |

*Positive control drug;
*1 50% effective dose;
*2 50% cell inhibitory (cytotoxic) concentration;
*3 selective index: $IC_{50}/EC_{50}$ Amentoflavone (1) (I-3'–II-8 biapigenin), volkensiflavone (5) (naringenin I-3–II-8 apigenin), volkunsiflavone hexamethyl ether and succedaneaflavanone (11) (I-6–II-6 binaringenin) also exhibited favorable antiviral activity against influenza B, having SI values of 178, 34, 38, and 15, respectively in the CPE assay. Agathisflavone (2) (I-6–II-8 biapigenin) and rhusflavanone (9) (I-6–II-8 binaringenin) demonstrated activity against influenza B virus, with SI values of 5.6 and 9.3, for the CPE assay. However in neutral red uptake tests, these biflavanoids showed no significant activity. None of the other biflavinoids assayed contributed significant activity. Methylation of volkensiflavone (5), to volkensiflavonone hexamethyl ether (6) led to lower activity and decreased cytotoxicity.

All of these biflavanoids were relatively inactive toward parainfluenza type 3, respiratory synecytial, measles, and adenovirus type 5 viruses, as shown in Table 7 and Table 8, except amentoflavone (1) and rhusflavanone (9) which exhibited some slight activity against respiratory syncytial virus and measles virus, respectively.

TABLE 7

| | Measles Virus | | | | | | Adenovirus Type 5 | | | | | |
|---|---|---|---|---|---|---|---|---|---|---|---|---|
| | CPI Inhibition | | | Neutral Red | | | CPE Inhibition | | | Neutral Red | | |
| Sample | $EC_{50}^{*1}$ μg/ml | $IC_{50}^{*2}$ μg/ml | $SI^{*3}$ | $EC_{50}^{*1}$ μg/ml | $IC_{50}^{*2}$ μg/ml | $SI^{*3}$ | $EC_{50}^{*1}$ μg/ml | $IC_{50}^{*2}$ μg/ml | $SI^{*3}$ | $EC_{50}^{*1}$ μg/ml | $IC_{50}^{*2}$ μg/ml | $SI^{*3}$ |
| Ribavirin* | 3 | 150 | 50 | 1 | 150 | 150 | — | — | — | — | — | — |
| HPMPA* | — | — | — | — | — | — | 30 | 80 | 3 | 8 | 40 | 5 |
| Amentoflavone (1) | <40 | <10 | 0 | <20 | <60 | 3 | >100 | 8 | 0 | >100 | 74 | 0 |
| Agathisflavone (2) | <60 | <10 | 0 | <10 | <30 | 3 | 15 | 18 | 1 | 22 | 37 | 1 |
| Robustaflavone (3) | <14 | <14 | 1 | <30 | <>100 | 1 | >100 | 56 | 0 | >100 | 102 | 0 |
| Hinokiflavone (4) | <3 | <4 | 1 | <5 | <11 | 2 | >10 | 22 | 0 | 19 | 27 | 1 |
| Volkensiflavone (5) | <12 | <10 | 1 | <6 | <10 | 1 | 56 | 47 | 1 | >32 | 30 | 0 |
| Volkensiflavone hexamethyl ether (6) | <70 | <60 | 1 | <7 | <13 | 1 | >100 | 47 | 0 | >100 | 50 | 0 |
| Rhusflavanone (9) | 14 | 21 | 2 | 5 | 40 | 8 | 56 | 47 | 1 | 33 | 15 | 0 |
| Rhusflavanone hexaacetate (10) | ><3 | <4 | 0 | <10 | <11 | 0 | >10 | 22 | 0 | 19 | 26 | 1 |
| Succedaneaflavone (11) | ><32 | <23 | 0 | <12 | <20 | 1 | 10 | 22 | 0 | 19 | 27 | 1 |
| Succedaneaflavone hexaacetate (12) | ><32 | <4 | 0 | <2 | <200 | <1 | 20 | 19 | 1 | 6 | 6 | 1 |

*Positive control drug;
*1 50% effective dose;
*2 50% cell inhibitory (cytotoxic) concentration;
*3 selective index: $IC_{50}/EC_{50}$

TABLE 8

| | Parainfluenza Type 3 Virus | | | | | | Respiratory Syncytial Virus | | | | | |
|---|---|---|---|---|---|---|---|---|---|---|---|---|
| | CPI Inhibition | | | Neutral Red | | | CPE Inhibition | | | Neutral Red | | |
| Sample | EC$_{50}$[1] µg/ml | IC$_{50}$[2] µg/ml | SI[3] | EC$_{50}$[1] µg/ml | IC$_{50}$[2] µg/ml | SI[3] | EC$_{50}$[1] µg/ml | IC$_{50}$[2] µg/ml | SI[3] | EC$_{50}$[1] µg/ml | IC$_{50}$[2] µg/ml | SI[3] |
| Ribavirin* | 25 | 245 | 10 | 17 | 331 | 19 | 12 | 120 | 10 | 6 | 60 | 10 |
| Amentoflavone (1) | >100 | ~56 | 0 | ~32 | ~56 | 2 | ~10 | ~56 | 6 | ~21 | ~35 | 2 |
| Agathisflavone (2) | >100 | ~33 | 0 | >100 | ~34 | 0 | >10 | ~8 | 0 | ~24 | ~15 | 0 |
| Robustaflavone (3) | >100 | 56 | 0 | 39 | 79 | 2 | >100 | ><56 | 0 | ~50 | ><100 | 2 |
| Hinokiflavone (4) | >1 | 1 | 0 | 5 | 7 | 1 | >3.2 | 2.5 | 0 | >3.2 | 6 | 0 |
| Volkensiflavone (5) | 47 | 50 | 1 | 15 | 44 | 3 | 32 | 56 | 2 | 28 | 13 | 0 |
| Volkensiflavone hexamethyl ether (6) | >32 | ~15 | 0 | >32 | ~33 | 0 | ~18 | ~30 | 2 | >32 | ~59 | >1 |
| Rhusflavanone (9) | >100 | 47 | 0 | 85 | 30 | 0 | >10 | 18 | 0 | 27 | 20 | 0 |
| Rhusflavanone hexaacetate (10) | >10 | 22 | 0 | 32 | 19 | 0 | >10 | 13 | 0 | 19 | 32 | 2 |
| Succedaneaflavone (11) | >10 | ~22 | 0 | 23 | ~29 | 0 | >10 | ~13 | 0 | ~16 | ~10 | 0 |
| Succedaneaflavone hexaacetate (12) | >10 | ~14 | 0 | >32 | ~13 | 0 | >3 | 4 | 0 | 6 | 6 | 1 |

*Positive control drug;
[1]50% effective dose;
[2]50% cell inhibitory (cytotoxic) concentration;
[3]selective index: IC$_{50}$/EC$_{50}$

EXAMPLE 8

Anti-HIV Viral Activity of Biflavanoids

We have investigated the anti-HIV-1 RT activity of biflavanoids isolated from *Rhus succedanea*, amentoflavone (1), agathisflavone (2), robustaflavone (3), hinokiflavone (4), rhusflavanone (9), succedaneaflavanone (11), and from *Garcinia multiflora*, volkensiflavone (5), morelloflavone (7), GB-1a (13), GB-1a 7"-O-β-glucoside (15), GB-2a (16), and their sulfate potassium salt, methyl ether, and acetyl derivative, volkensiflavone hexaacetate (6), morelloflavone heptamethyl ether (8), rhusflavanone hexaacetate (10), succedanea-flavanone hexaacetate (12), GB-1a hexamethyl ether (14), and robustaflavone tetrasulfate potassium salt (17).

Anti-HIV-1 RT Assay. The HIV-1 RT is a 66-kDa recombinant enzyme obtained in an *Escherichia coli* expression system using a genetically engineered plasmid; the enzyme was purified to near homogeneity. Synthetic DNA segments were used to introduce initiation and termination codons into the HIV-1 RT coding sequence, which permits expression of large quantities of HIV-1 RT in *E. coli*. The enzyme was shown to be active in RT assays and exhibited inhibitory properties with several known antiretroviral agents (e.g. AZT and suramin) that were indistinguishable from the viral enzyme. The purified recombinant enzyme was sufficiently similar to the viral enzyme that it can be substituted for the latter in drug screening assays. The recombinant HIV-1 RT preparation used in all experiments had a protein concentration of 0.11 mg/mL and an activity of 238 nmol TTP incorporated per 10 min per mg of protein at 37° C. Prior to performing an experiment, the enzyme was diluted tenfold with buffer analogous to that used in the assay.

The assay mixture (final volume 100 µL) contained the following: 50 mM Tris-HCl buffer (pH 8.0), 150 mM KCl, 5 mM MgCl$_2$, 0.5 mM ethylene glycol-bis-(β-aminoethylether)-N,N'-tetraacetic acid (EGTA), 5 mM dithiothreitol, 0.3 mM glutathione, 2.5 µg/mL bovine serum albumin, 41 µM poly A [Σ260 (mM)=7.8], 9.5 µM oligo (dT),12–18 [Σ265(µM)=5.6], 0.05% Triton X-100, 20 µM TTP, and 0.5 µCi of [$^3$H]TTP. The reaction was started by the addition of 10 AL of HIV-1 RT, and the mixture was permitted to incubate at 37° C. for 1 h. Reactions were terminated by the addition of 25 µL of 0.1 M EGTA followed by chilling in ice. Aliquots of each reaction mixture (100 µL) were then spotted uniformly onto circular 2.5 cm DE-81 (Whatman) filters, kept at ambient temperature for 15 minutes, and washed four times with 5% aqueous Na$_2$HPO$_4$.7H$_2$O. This was followed by two more washings with doubly distilled H$_2$O. Finally, the filters were thoroughly dried and subjected to scintillation counting in a nonaqueous scintillation fluid.

For testing enzyme inhibition, five serial dilutions of samples in DMSO (10 µL) were added to the reaction mixtures prior to the addition of enzyme (10 µL). The final DMSO concentration used was 10%. The highest concentration of pure natural products and plant extracts tested was 200 µg/mL. Control assays are performed without the compounds or extracts, but an equivalent volume of DMSO was added. Fargaronine chloride was used as the positive control substance. This compound was isolated from *Fagara xanthoxyloides* Lam. Other positive control substances used were suramin (IC$_{50}$ 18 µg/mL) and daunomycin (IC$_{50}$ 125 µg/mL). The assay procedure and the concentration of all components were the same as that mentioned above.[47]

Anti-HIV-1 RT Assay in Primary Human Lymphocytes

Cell Culture. Human PBM cells from healthy HIV-1 seronegative and hepatitis B virus seronegative donors were isolated by Ficoll-Hypaque discontinuous gradient centrifugation at 1,000×g for 30 min, washed twice with phosphate-buffered saline (pH 7.2, PBS), and pelleted by centrifugation at 300×g for 10 min. Before infection, the cells were stimulated by phytohemagglutinin (PHA) at a concentration of 6 µg/mL for 2–3 days in RPMI 1640 medium, supplemented with 15% heat-inactivated fetal calf serum, 1.5 mM L-glutamine, penicillin (100 U/mL), streptomycin (100 µg/mL), and 4 mM sodium bicarbonate buffer.

Viruses. HIV-1 (strain LAV-1) was obtained from Dr. P. Feorino (Emory University, Atlanta, Ga.). The virus was propagated in human PBM cells using RPMI 1640 medium, as described previously[58] without PHA or fungizone and supplemented with 26 units/mL of recombinant interleukin-2 (Cetus Corporation, Emeryville, Calif.) and 7 μg/mL DEAE-dextran (Pharmacia, Uppsala, Sweden). Virus was obtained from cell-free culture supernatant and was titrated and stored in aliquots at −70° C. until use.

Inhibition of Virus Replication in Human PBM Cells. Uninfected PHA-stimulated human PBM cells were infected in bulk with a suitable dilution of virus. The mean reverse transcriptase (RT) activity of the inocula was about 60,000 dpm RT activity/106 cells/10 mL. This represents, by a limiting dilution method in PBM cells, a multiplicity of infection of about 0.01. After 1 h, the cells were uniformly distributed among 25 cm² flasks to give a 5 mL suspension containing about 2×10⁶ cells/mL each. The samples at twice their final concentration in 5 mL of RPMI 1640 medium, supplemented as described above, were added to the cultures. The cultures were maintained in a humidified 5% $CO_2$—95% air incubator at 37° C. for six days after injection, at which point all cultures were sampled for supernatant RT activity. Previous studies had indicated that maximum RT levels were obtained at that time.

RT Activity Assay. A volume of supernatant (1 mL) from each culture was clarified of cells at 300×g for 10 min. Virus particles were pelleted at 12,000 rpm for 2 h using a Jouan refrigerated microcentrifuge (Model MR 1822) and suspended in 100 μL of virus disrupting buffer (50 mM Tris-HCl, pH 7.8, 800 mM NaCl, 20% glycerol, 0.5 mM phenylmethyl sulfonyl fluoride, and 0.5% Triton X-100).

The RT assay was performed in 96-well microtiter plates, as described by Spira.[69] The reaction mixture, which contained 50 mM Tris-HCl, pH 7.8, 9 mM $MgCl_2$, 5 mM dithiothreitol, 4.7 μg/ML (rA)n(dT)12–18, 140 μM dAPT, and 0.22 μM [³H]TTP (specific activity 78.0 Ci/mmol, equivalent to 17,300 cpm/pmol; NEN Reserch Products, Boston, Mass.), was added to each well. The sample (20 μL) was added to the reaction mixture, which was then incubated at 37° C. for 2 h. The reaction was terminated by the addition of 100 μL of 10% trichloroacetic acid (TCA) containing 0.45 mM sodium pyrophosphate. The acid-insoluble nucleic acids which precipitated were collected on glass filters using a Skatron semi-automatic harvester (setting 9). The filters were washed with a 5% TCA and 70% ethanol, dried and placed in scintillation vials. Scintillation fluid (Ecolite, ICN, Irvine, Calif.) (4 mL) was added and the amount of radioactivity in each sample was determined using a Beckman liquid scintillation analyzer (Model LS 3801). The results were expressed in dpm/mL of original clarified supernatant. The procedures for the anti-HIV assays in PBM cells described above have been published.[67,69]

Cytotoxicity Studies in PBM Cells. The compounds were evaluated for their potential toxic effects on uninfected PHA-stimulated human PBM cells. The cells were cultured with and without drug for 24 h, at which time radiolabeled thymidine was added. The assay was performed as described previously.[35] Alternately, cells are counted on day 6 using a hemacytometer and/or Coulter counter as described previously.[68]

Median-Effect Method. $EC_{50}$ and $IC_{50}$ values were obtained by analysis of the data using the median-effect equation.[42] These values were derived from the computer-generated median effect plot of the dose-effect data using a commercially available program.[43]

The results shown in Table 9 indicate that both hinokiflavone (4) and robustaflavone (3) demonstrated similar activity against HIV-1 RT at an $IC_{50}$ (50% inhibition dose) of 35.2 μg/mL and 33.7 μg/mL, respectively. The water soluble form of robustaflavone, robustaflavone tetrasulfate K-salt (17) exhibited 95.5% inhibition at a concentration of 200 μg/mL, with an $IC_{50}$ value of 144.4 μg/mL. Amentoflavone (1), agathisflavone (2), morelloflavone (7), GB-1a (13), and GB-2a (16) were moderately active against HIV-1 RT with $IC_{50}$ values of 64.0 μg/mL, 53.8 μg/mL, 64.7 μg/mL, 127.8 μg/mL, and 94.6 μg/mL, respectively. The other biflavanoids were either slightly active or inactive against HIV-1 RT.

The results of both studies are presented in Table 9. The results of the inhibitory activity tests using HIV-1 RT enzyme (p66/p51 heterodimer) indicated that the biflavones, two apigenin units linked either with C—C or C—O—C bonds, exhibited significant activity. Robustaflavone (3) (two apigenins linked through an I-6–II-3' linkage) and hinokiflavone (4) (I-6-O-II-4' linkage) demonstrated similar activity, with 50% inhibition ($IC_{50}$) at doses of 35.2 μg/mL and 33.7 μg/mL, respectively. The $IC_{50}$ values of amentoflavone (1) (I-8–II-3' linkage) and agathisflavone (2) (I-6–II-8 linkage) were 64.0 μg/mL and 53.8 μg/mL, respectively.

TABLE 9

Anti-HIV-1 RT Activity of Biflavanoids

| Compounds | Anti-HIV-1 RT % Inhibition at 200 μg/ml | $IC_{50}$ μmL (μM) | Ant-HIV-1 in PBM cells $EC_{50}$ (μM) | Cytotoxicity in PBM cells $IC_{50}$ (μM) | Selective Index (SI) |
|---|---|---|---|---|---|
| Apigenin | 72 | 120 (443) | | | |
| Naringenin | 34.9 | weakly active | | | |
| Amentoflavone (1) | 97.3 | 64.0 (118.8) | >10.94 | 35 | |
| Agathisflavone (2) | 99.8 | 53.8 (99.9) | 7.3, 6.0 | 25 | 0.37~3 |
| Robustaflavone (3) | 91.4 | 35.2 (65.4) | >100 | 77 | 0.4~3 |
| Hinokiflavone (4) | 89.0 | 33.7 (61.8) | 4.1 | 9.1 | ND |
| Volkensiflavone (5) | 45.3 | Weakly active | | | 2.2 |
| Volkensiflavone $Me_2$ (6) | 0.00 | inactive | | | |
| Morelloflavone (7) | 99.2 | 64.7 (116.3) | 5.7, 8.0 | 82 | 10~14 |
| Rhusflavanone (9) | 14.1 | inactive | | | |

TABLE 9-continued

Anti-HIV-1 RT Activity of Biflavanoids

| Compounds | Anti-HIV-1 RT % Inhibition at 200 µg/ml | Anti-HIV-1 RT $IC_{50}$ µmL (µM) | Ant-HIV-1 in PBM cells $EC_{50}$ (µM) | Cytotoxicity in PBM cells $IC_{50}$ (µM) | Selective Index (SI) |
|---|---|---|---|---|---|
| Rhusflavanone Ac$_6$ (10) | 0.00 | inactive | | | |
| Succedaneaflavanone (11) | 22.1 | inactive | | | |
| Succedaneaflavanone Ac$_6$ (12) | 0.00 | inactive | | | |
| GB-1a (13) | 86.0 | 127.8 (235.6) | >10.38 | 88 | 2.8~8 |
| GB-1a Me$_6$ (14) | 0.00 | inactive | | | |
| GB-1a glucoside (15) | 1.46 | inactive | | | |
| GB-2a (16) | 96 | 94.6 (169.5) | | | |
| Robustaflavone tetrasulfate K-salt | 95.5 | 144.4 | | | |

Biflavanoids constructed of flavanone-flavone units through I-3–II-8 linkages were moderately to weakly active, i.e. morelloflavone (7) (naringenin I-3–II-8 quercetin) demonstrated moderate activity, with an $IC_{50}$ value of 64.7 µg/mL, while volkensiflavone (5)(narnigenin I-3–II-8 apigenin) was weakly active. Biflavanones consisting of two naringenin units or naringenin-eriodictol through I-3–II-8 linkages exhibited moderate activity, such as GB-1a (13) ($IC_{50}$ 127.8 µg/mL) and GB-2a (16) ($IC_{50}$ 94.6 µg/mL). Biflavanones such as rhusflavanone (9) and succedaneaflavanone (11), comprised of two naringenin units linked through either I-6–II-8 or I-6–II-6 linkages, were completely inactive.

Other structural characteristics were related to activity in our study. Methylation of the hydroxyl groups of the biflavanoids resulted in diminished activity. For instance, morelloflavone heptamethyl ether (8), volkensiflavone hexamethyl ether (6), and GB-1a hexamethyl ether (14), were inactive; all had exhibited moderate activity before alkylation. The fact that GB-1a-7"-O-glucoside (15), demonstrated no activity indicated that the 7"-hydroxyl group was especially important for anti-HIV-1 RT activity.

Six biflavanoids that were determined to be active in the HIV-1 RT enzyme assay were tested in human PBM cells infected with HIV-1 (strain LAV). These results are presented in Table 9. It has been observed that, although robustaflavone (3) exhibited significant inhibitory activity in the HIV-1 RT enzyme assay, it was found to be inactive in the assay for the PMB cells infected with HIV-1. However morelloflavone (7), in the whole cell assay, exhibited potent inhibitory activity with an $EC_{50}$ (50% effective dose) value of 5.7 (8.0) µg/mL. Morelloflavone only possessed moderate activity in the anti-HIV-1 RT assay ($IC_{50}$ 64.7 µg/mL; 116.3 µM). This may suggest that the activity of these biflavanoids may be dependent upon different cellular mechanisms.

Other active compounds were hinokiflavone (4) and GB-1a (13), which exhibited good activity inhibiting viral replication in human PBM cells, but also high toxicity against uninfected PHA-stimulated human PBM cells. The other compounds (amentoflavone (1) and agathisflavone (2)) assayed in PMB cells appeared to either lack antiviral potency or display poor selectivity. From these results, it was concluded that biflavanoids comprised of flavanone (naringenin) and flavone (luteolin) via a I-3–II-8 bond demonstrate the most promising anti-HIV-1 activity.

In the past, some monoflavanoids have been reported to demonstrate anti-HIV activity. Baicalein (5,6,7-trihydroxyflavone), tiliroside (kaempferol 3-β-D (6"-p-coumaroyl)glucoside), quercetin (3,3',4',5,7-pentahydroxyflavone), kaempferol (3,4',5,7-tetrahydroxyflavone), and quercetagetin (3,3',4',5,6,7-hexahydroxyflavone) exhibited inhibitory activity against HIV-1 reverse transcriptase, whereas luteolin (3',4',5,7-tetrahydroxyflavone) and apigenin (4',5,7-trihydroxyflavone) showed moderate to slight inhibition, and naringenin (4',5,7-trihydroxyflavanone) was completely inactive. [63,64,70] This revealed that the presence of both the unsaturated double bond between positions 2 and 3 of the flavonoid pyrone ring (e.g. flavone), and either the 3 hydroxyl groups introduced at the 5, 6, and 7 positions (bicalein) or the 3, 3', and 4' positions (quercetin) were a prerequisite for inhibition of RT activity.

In our study, apigenin exhibited moderate activity and naringenin demonstrated slight inhibition. Biflavanoids which consisted of two apigenin units (amentoflavone (1), agathisflavone (2), robustaflavone (3), and hinokiflavone (4)) demonstrated significant activity. Biflavanoids constructed of flavanone and flavone units (morelloflavone (7)) and biflavanone, linked through I-3–II-8 (GB-1a (13) and GB-2a (16)) were moderately active, and biflavanones linked through ring A of two naringenin units (rhusflavanone (9) and succedaneaflavanone (11)) were inactive. This structure-activity comparison again demonstrates that hydroxyl groups and at least one flavone unit in the biflavanoids are required for activity. A I-3–II-8 linkage is also necessary for biflavanones to exhibit activity. A further conclusion is that previously active compounds become inactive when hydroxy groups are methylated.

EXAMPLE 9

Anti-Herpes Viral Activity of Biflavanoids

Anti-Herpes Viral Assay: The viruses used in the primary screen for anti-viral activity against herpes viruses consisted of: Herpes Virus 1 (HSV-1 E-377 strain), Herpes Virus 2

(HSV-2 MS strain), Cytomegalovirus (HCMV AD 169 strain), Varicella Zoster Virus (VZV Ellen Strain), and Epstein-Barr Virus (EBV), superinfection of Raji or Daudi cells with P3HR-1.

The assay for the inhibition of the cytopathic effect (CPE) for HSV, HCMV and VZV was as follows: Low passage human foreskin fibroblast cells were seeded in 96-well tissue culture plates 24 h prior to use, at a cell concentration of $2.5\times10^4$ cells/mL in 0.1 L of minimal essential medium (MEM) supplemented with 10% fetal bovine serum (FBS). The cells were then incubated for 24 h at 37° C. in a $CO_2$ incubator. After incubation, the medium was removed and 100 µL of MEM containing 2% FBS was added to all but the first row. In the first row, 125 µL of the test compound was added in triplicate wells. Medium alone was added to both cell and virus control wells. The test compound in the first row was diluted serially 1:5 throughout the remaining wells by transferring 25 µL using a Cetus Liquid Handling Machine. After dilution of the compound, 100 µL of the appropriate virus concentration was added to each well, excluding cell control wells which received 100 µL of MEM. For HSV-1 and HSV-2 assays, the virus concentration utilized was 1000 PFUs per well. For CMV and VZV assays, the virus concentration added was 2500 PFUs per well. The plates were then incubated at 37° C. in a $CO_2$ incubator for three days for HSV-1 and HSV-2, 10 days for VZV, or 14 days for CMV. After the incubation period, the media was aspirated and the cells stained with a 0.1% crystal violet solution for 30 min. The stain was then removed and the plates rinsed using tap water until all the excess stain was removed. The plates were allowed to dry for 24 h and then read on a Skatron Plate reader at 620 nm.

VZV Plaque Reduction Assay. Two days prior to use, HFF cells were plated into six-well plates and incubated at 37° C., with 5% $CO_2$ atmosphere and 90% humidity. On the date of assay, the test compound was made up at twice the desired concentration in 2X MEM using six concentrations of the compound. The initial starting concentrations were usually from 200 µg/mL to 0.06 µg/mL. The VZV was diluted in 2X MEM containing 10% FBS to a desired concentration which would give 20–30 plaques per well. The media was then aspirated from the wells and 0.2 mL of the virus was added to each well in duplicate, with 0.2 mL of media being added to the drug toxicity wells. The plates were then incubated for 1 h with shaking every 15 min. After the incubation period, mean equal amount of 1% agarose was added to an equal volume of each test compound dilution. This provided final test compound concentrations beginning with 100 µg/mL and ending with 0.03 µg/mL, and a final agarose overlay concentration of 0.5%. The test compound agarose mixture was applied to each well in 2 mL volumes. The plates were then incubated, the stain aspirated, and plaques counted using a stereomicroscope at 10x magnification for ten days, after which the cells were stained with a 1.5% solution of neutral red dye. On days three and six an additional 1 mL overlay with equal amounts of 2X MEM and 1% agarose were added. At the end of the 4–6 h incubation period, the stain was aspirated and plaques counted using a stereomicroscope at 10x magnification.

Herpes Viruses (HSV-1, HSV-2, HCMV, VZV, and EBV)

The results of the anti-herpes viruses activity assays of these biflavanoids are presented in Table 10. Among the compounds studied, only robustaflavone (3) exhibited significant inhibitory activities against HSV-1 and HSV-2 viruses. Activity values are measured by effective concentration ($EC_{50}$) and cytotoxicity concentration ($CC_{50}$) at which 50% of cells are free from pathogens or 50% of cells die. The values for robustaflavone (3) are an $EC_{50}$ of 8.6 µg/mL and $CC_{50}$>100 µg/mL, which results in a selectivity index of >11.6. The anti-viral activity of robustaflavone (3) against HSV-2 produced an $EC_{50}$ value of 8.5 µg/mL, a $CC_{50}$ of >100 µg/mL, and a SI of 11.8. Other results include amentoflavone (1) which demonstrated only slight activity against HSV-1. Volkensiflavone (5) exhibited weak inhibitory activity against both HCMV and VZV. Methylation of volkensiflavone (5) into volkensiflavone hexamethyl ether (6), resulted in the loss of activity, and a decrease in toxicity against HCMV, but an increase in activity and toxicity against VZV. Acetylation of rhusflavanone (9) to rhusflavanone hexaacetate (10) increased the activity and toxicity against HSV-1 and HSV-2. Acetylation of succedaneaflavanone (11) into succedaneaflavanone hexaacetate (12) led to a slight decrease of both activity and toxicity, and resulted in almost equal SI values. When assayed for activity against VZV, the acetylation product (12) resulted in an SI value which increased from <3 to 9.6.

TABLE 10

| | HSV-1 (HFF Cells) CPE Inhibition | | | HSV-2 (HFF Cells) CPE Inhibition | | | HCMV (HFF Cells) CPE Inhibition | | | VZV (HFF Cells) Plaque Reduction | | |
|---|---|---|---|---|---|---|---|---|---|---|---|---|
| Sample | $EC_{50}^{*1}$ µg/ml | $CC_{50}^{*2}$ µg/ml | $SI^{*3}$ | $EC_{50}^{*1}$ µg/ml | $CC_{50}^{*2}$ µg/ml | $SI^{*3}$ | $EC_{50}^{*1}$ µg/ml | $CC_{50}^{*2}$ µg/ml | $SI^{*3}$ | $EC_{50}^{*1}$ µg/ml | $CC_{50}^{*2}$ µg/ml | $SI^{*3}$ |
| ACT* | 1.5 | — | | 0.9 | >100 | | | | | 0.5 | | |
| GVC* | — | >100 | | — | | | .4 | >100 | | | | |
| Amentoflavone (1) | 17.9 | >100 | >5.6 | 48.0 | >100 | >2.1 | 50.8 | >100 | >1.9 | >4.0 | 9.3 | <2.3 |
| Agathisflavone (2) | >100 | >100 | 0 | >100 | >100 | 0 | 94.8 | >100 | >1.0 | >4 | 12.0 | <3.0 |
| Robustaflavone (3) | 8.6 | >100 | >11.6 | 8.5 | >100 | >11.8 | 54.8 | >100 | >1.8 | | | |
| Hinokiflavone (4) | >20 | 77.7 | <3.9 | >20 | 77.7 | <3/9 | >0.8 | 2.6 | <3.2 | >4.0 | 16.8 | <4.2 |
| Volkensiflavone (5) | >100 | >100 | 0 | 87.9 | >100 | >1.1 | >4.0 | 16.8 | <4.2 | >20 | 80.0 | <4.0 |
| Volkensiflavone hexamethyl ether (6) | >100 | >100 | 0 | >100 | >100 | 0 | >100 | >100 | 0 | 3.3 | 11.1 | 3.4 |
| Rhusflavanone (9) | >100 | >100 | 0 | 15.7 | >100 | >6.4 | >4.0 | 13.7 | <3.4 | >4 | 16.0 | <4 |
| Rhusflavanone hexaacetate (10) | >4.0 | 18.5 | <4.6 | >4.0 | 18.5 | <4.6 | >4.0 | 13.4 | <3.3 | 11.3 | 46.7 | 4.1 |

TABLE 10-continued

| Sample | HSV-1 (HFF Cells) CPE Inhibition | | | HSV-2 (HFF Cells) CPE Inhibition | | | HCMV (HFF Cells) CPE Inhibition | | | VZV (HFF Cells) Plaque Reduction | | |
|---|---|---|---|---|---|---|---|---|---|---|---|---|
| | $EC_{50}^{*1}$ μg/ml | $CC_{50}^{*2}$ μg/ml | $SI^{*3}$ | $EC_{50}^{*1}$ μg/ml | $CC_{50}^{*2}$ μg/ml | $SI^{*3}$ | $EC_{50}^{*1}$ μg/ml | $CC_{50}^{*2}$ μg/ml | $SI^{*3}$ | $EC_{50}^{*1}$ μg/ml | $CC_{50}^{*2}$ μg/ml | $SI^{*3}$ |
| Succedaneaflavone (11) | >20 | 60.7 | <3.0 | >20 | 60.7 | <3.0 | >20 | 55.5 | <2.7 | >20 | 60.0 | <3.0 |
| Succedaneaflavanone hexaacetate (12) | >4 | 17.7 | <4.4 | >4.0 | 17.7 | <4.4 | >4.0 | 14.4 | <3.5 | 7.1 | 68.0 | 9.6 |

*Positive control drug;
*¹50% effective dose;
*²50% cell inhibitory (cytotoxic) concentration;
*³selective index: $CC_{50}/EC_{50}$

EXAMPLE 10

In Vivo Evaluation of Robustaflavone in a Murine Influenza Model

In this Example, a series of in vivo experiments were run to determine if robustaflavone is efficacious against an experimentally induced influenza virus infection in mice. Prior to beginning this study, a series of preliminary experiments were run to determine the maximum tolerated dose of this compound in mice. Since the compound is not soluble in aqueous medium, it was suspended in 0.4% carboxymethylcellulose (CMC), a vehicle commonly used for water-insoluble compounds. When it was found that the compound was well tolerated at high dosages in this suspension, the question arose as to whether it was being adequately absorbed by the animal. Some studies were thus conducted using other vehicles in which the compound was more soluble. These vehicles included dimethylsulfoxide (DMSO), dimethyl formamide (DMF), and polyehtylene glycol (PEG).

Materials and Methods

Animals: Female 13–15 g specific pathogen-free BALB/c mice were obtained form Simonsen Laboratories (Gilroy, Calif.). They were quarantined 24 h prior to use, and maintained on Wayne Lab Blox and tap water. After being infected, their drinking water contained 0.006% oxytetracycline (Pfizer, New York, N.Y.) to control possible secondary bacterial infections.

Virus: A/NWS/33 (H1N1) was obtained from K. W. Cochran, Univ. of Michigan (Ann Arbor, Mich.). A virus pool was prepared in MDCK cells; this was titrated in mice, ampuled, and stored at −80° C. until used.

Compounds: Robustaflavone was stored at room temperature until used. Ribavirin, used as a positive control, was obtained from ICN Pharmaceuticals (Costa Mesa, Calif.). Vehicles considered included DMSO (Sigma Chemical Co., St. Louis, Mo.), DMF (Sigma), PEG M.W. 200 (Aldrich Chemical Co. Milwaukee, Wis.), 0.4% CMC (Sigma) and 1-methyl-2-pyrrolidinone (MPD, Aldrich).

Arterial oxygen Saturation (SaO2) Determinations: $SaO_2$ was determined using the Ohmeda Blox 3740 pulse oximeter (Ohmeda, Louisville, Ohio)). The ear probe attachment was used, the probe placed on the thigh of the animal, with the slow instrument mode selected. Readings were made after a 30 second stabilization time on each animal. Use of this device for measuring effects of influenza virus on arterial oxygen saturation have been described by us.[72]

Lung Virus Determinations: Each mouse lung was homogenized and varying dilutions assayed in triplicate for infectious virus in MDCK cells as described previously.[73]

Experiment Design

1. Toxicity Determination of robustaflavone in CMC Vehicle: The compound was suspended in 0.4% CMC at a concentration of 37.5 mg/mL to make a dosage of 500 mg/kg/day. It was injected i.p. into 2 mice daily for 5 days. The mice were weighed and deaths noted daily.

2. Toxicity Determination of robustaflavone in 100% DMSO: The compound was dissolved in DMSO at a concentration of 25 mg/mL and in a later experiment in a concentration of 11.25 mg/mL to make dosages of 250 and 75 mg/kg/day, respectively. The higher dosage was injected i.p. into mice twice daily for 5 days in a volume of 0.1 mL/injection daily for 5 days in a volume of 0.05 mL/injection. As controls, mice were treated by the same treatment schedule with DMSO only in volumes of 0.1 or 0.05 mL/injection. Weight gain and mortality was determined in these animals.

3. Toxicity Determination of DMF and PEG only: DMF and PEG 200 in a concentration of 100% were injected i.p. into separate groups of mice daily for 5 days using a volume of 0.05 mL/injection. Again, effects on host weight and deaths of mice were monitored.

4. Effect of robustaflavone in CMC or in DMSO on influenza virus infection in mice. In the study with CMC, robustaflavone was used in dosages of 200 and 100 mg/kg/day; using DMSO vehicle; the dosages were 75 and 37.5 mg/kg/day, with the compound administered i.p. twice daily for 5 days beginning 4 h pre-virus exposure. The mice were used in each dose to monitor effects on $SaO_2$ and death; from an additional group of similarly infected and treated mice, 3 animals were killed on days 3, 5, 7 and 9 to assay for lung score (0=normal, 4=maximal consolidation), weight, and virus titer. Three to four mice were used as toxicity controls, which were weighed prior to treatment and again 18 h after treatment termination, and deaths noted daily. Ribavirin, dissolved in saline, was used in a dose of 75 mg/kg/day with the same treatment schedule. Three sets of virus controls were used: Infected-untreated, infected-treated with CMC only, and infected-treated with DMSO only. Twenty animals were used in each of these control groups to monitor $SaO_2$ and death, with 3 additional mice taken in parallel with treated animals to determine effects on lung consolidation and virus titer. Two sets of normal controls were used; one group of three mice was weighed and held in parallel with the toxicity controls. From the second group three mice were killed on days 3 and 9 for comparison of lung score and weight.

Statistical Evaluation: Increase in survivor number was evaluated using chi square analysis with Yates' correction.

Mean survival time increases, virus titer and $SaO_2$ value differences were analyzed by t-test. Lung consolidation scores were evaluated by ranked sum analysis.

Results and Discussion

Toxicological Effects on Various Vehicles: The results of the various experiments with the vehicles considered are summarized in Table 11. CMC was the most well tolerated, followed by DMSO. DMF and PEG 200 were lethally toxic to the mice. One mouse died immediately following the day 4 i.p. treatment with DMSO; since this animal died instantly it is probable the death was due to penetration of an organ by the needle as it was administered into the peritoneal cavity. Using the 0.05 mL volume of DMSO, the animals appeared to tolerate this vehicle better than at 0.1 mL. DMF was highly lethal, killing both animals after two injections, and PEG 200 was only slightly better, with all mice dying after 3 injections.

Based on the above data, both CMC and DMSO were used as solvents for robustaflavone, the latter used in injection volumes of 0.05 mL.

Dose Range-Finding Studies with Robustaflavone in Mice: Using CMC as vehicle, robustaflavone appeared to be quite insoluble, with dense yellow particulate material seen in the formulation. When injected i.p. twice daily for 5 days, a dose of 200 mg/kg/day appeared reasonably well tolerated, the treated animals surviving therapy but losing 0.1 g of weight in the 5-day treatment period. The material was very soluble in DMSO, forming a clear solution. A 250 mg/kg/day dose injected i.p. twice daily for 5 days was lethally toxic to the mice, all animals dying by day 5 of treatment and a 6 g weight loss seen. The injection volume in this experiment was 0.1 mL, when the experiment was repeated using 0.05 mL injection volume, the dosage was lowered to 75 mg/kg/day. At this dose, all mice survived, although they lost 2 g of weight during the 5-day treatment period.

The data using CMC as vehicle suggests the compound was not being well absorbed in the animal, so for the antiviral experiment it was decided to use doses of 200 and 100 mg/kg/day. The DMSO studies indicated 75 mg/kg/day may be approaching the maximum tolerated dose, so that dose and 37.5 mg/kg/day were chosen for the in vivo antiviral experiment.

Effect of robustaflavone in DMSO on Influenza A Virus Infections in Mice: The results of this experiment are summarized in Table 12 and FIG. 1 through 4. It was found that the 75 mg/kg/day dose in this antiviral experiment was lethally toxic to the mice; the 37.5 mg/kg/day dose killed 2 of 3 toxicity control mice as well. Due to this apparent toxicity, the effects on survivors and $SaO_2$ values were inconclusive. This excess toxicity did not correlate with the earlier-run range-finding study, although in the latter study marked weight loss was seen suggesting the compound was approaching a lethally toxic dose.

Figure 2:
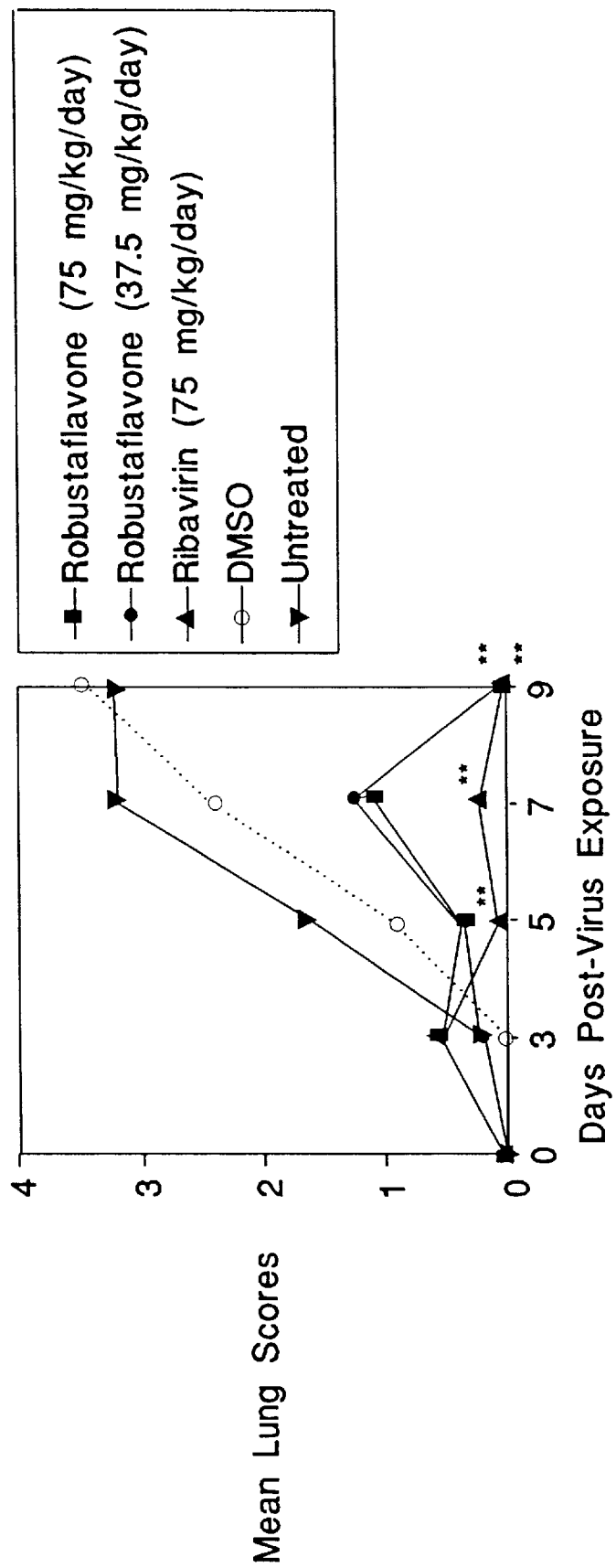
FIG. 2 illustrates the effect of treatment with robustaflavone in DMSO on mean lung scores in Influenza A virus-infected mice as described in Example 10.
Figure 3:
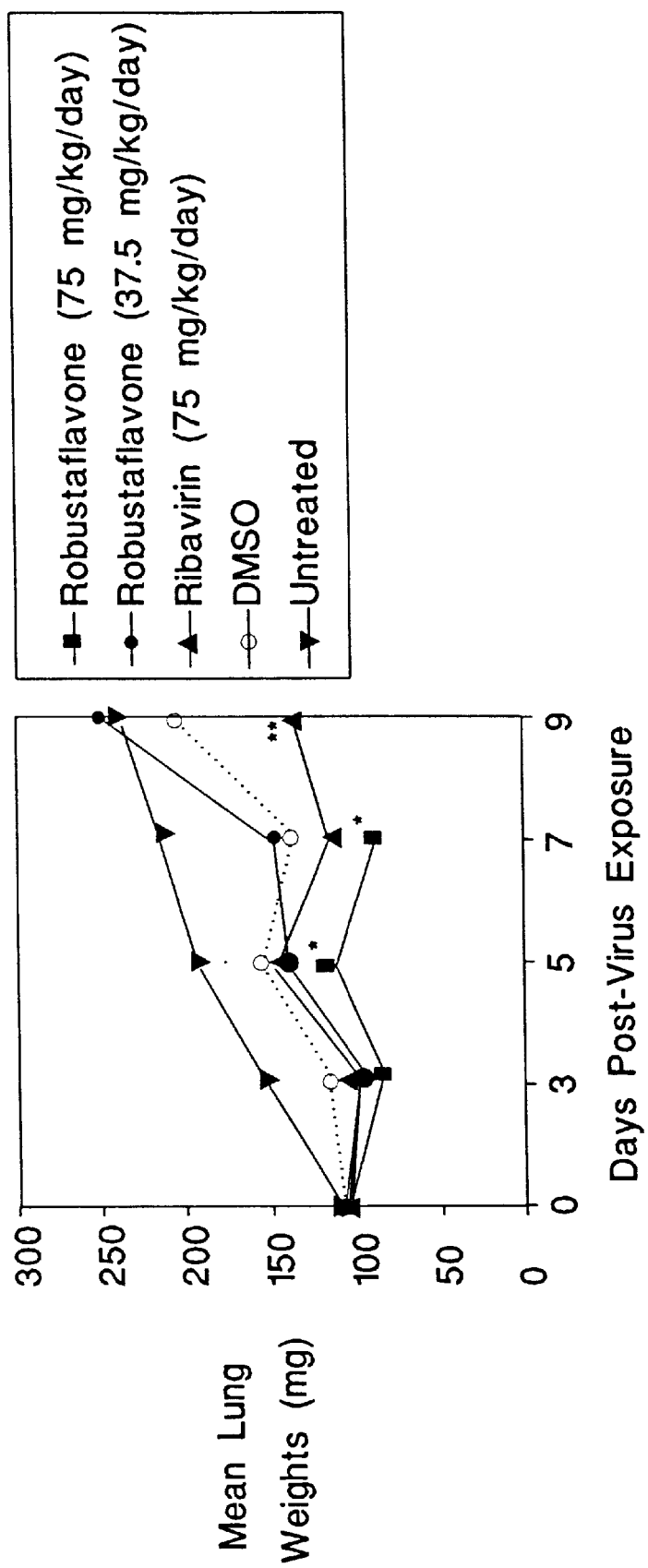
FIG. 3 illustrates the effect of treatment with robustaflavone in DMSO on mean lung weights in Influenza A virus-infected mice as described in Example 10.
Figure 4:
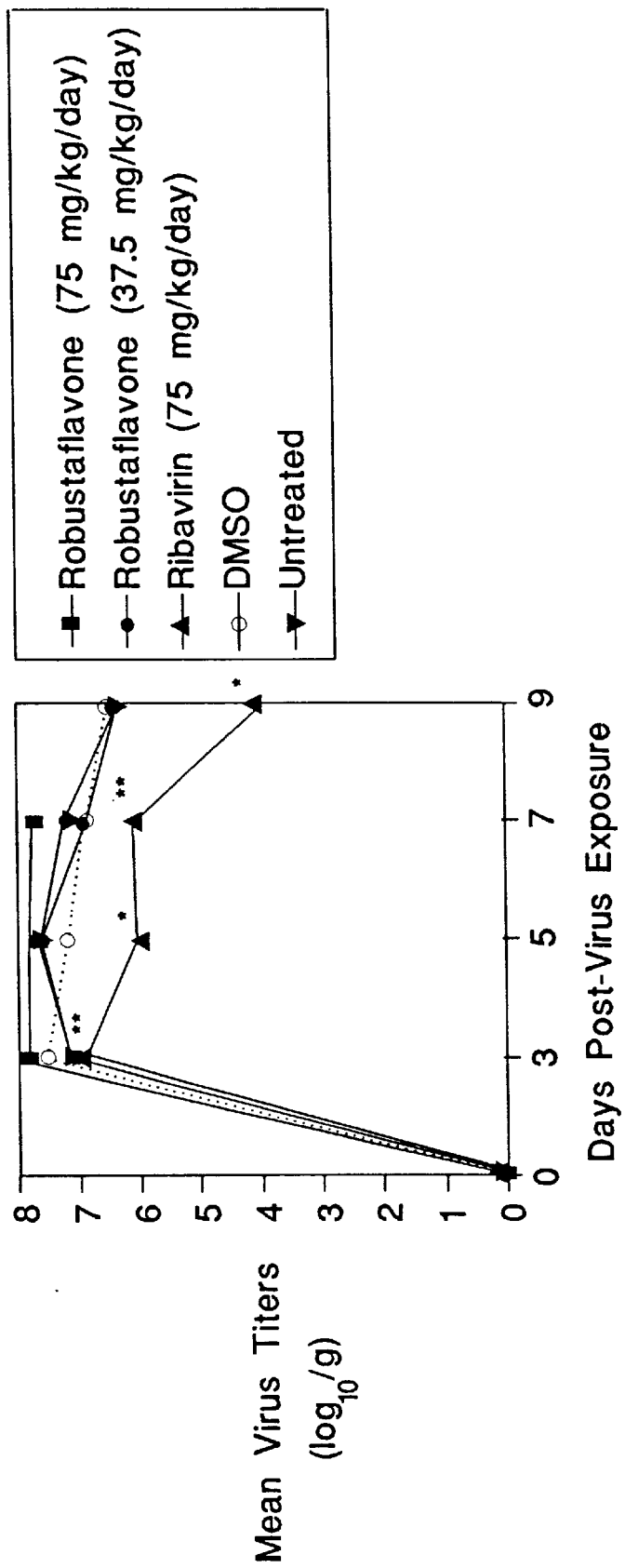
FIG. 4 illustrates the effect of treatment with robustaflavone in DMSO on mean virus titers in Influenza A virus-infected mice as described in Example 10.

A review of FIG. 2 and 3, showing effects of treatment on lung scores and lung weights, indicates a significant effect of this compound on lowering lung scores and weights. This effect was dose-responsive, and suggests robustaflavone may have a significant influenza-inhibitory effect which may also be seen at a dose more well tolerated to the mice.

DMSO used alone was not lethal to the mice, but infected animals treated with DMSO only died approximately 2 days sooner than untreated infected controls (Table 12). This suggests the DMSO injection may result in an enhancement of the infection.

Ribavirin, run in parallel as a positive control, was highly active in inhibiting the infection using all evaluation parameters.

Figure 5:
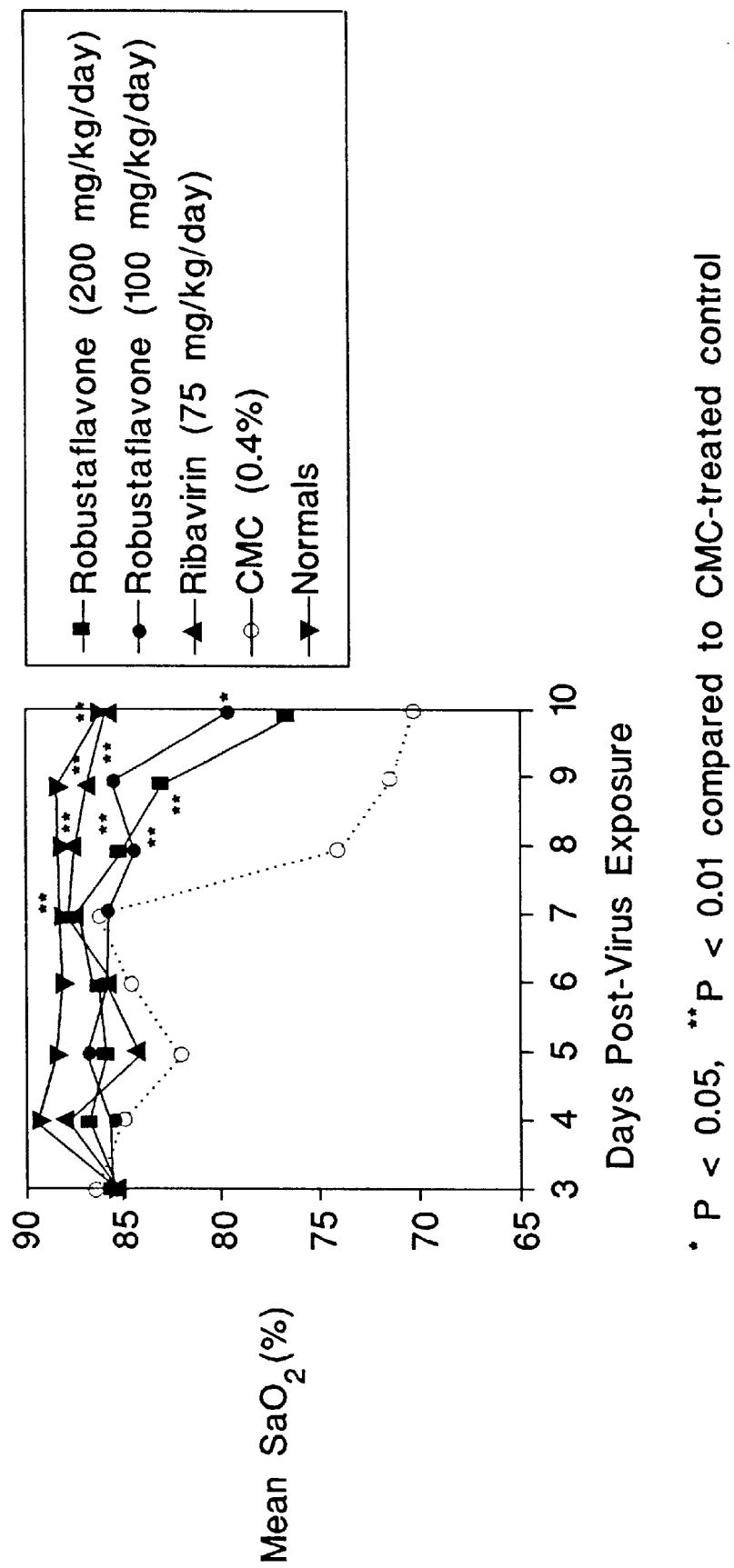
FIG. 5 illustrates the effect of treatment with robustaflavone in CMC on mean arterial oxygen saturation (mean $SaO_2$ (%)) in Influenza A virus-infected mice as described in Example 10.

Effect of robustaflavone in CMC on influenza A virus infections in mice: The results of this study are seen in Table 13 and in FIGS. 5 through 8. Robustaflavone appeared to be well tolerated in this experiment, with all toxicity controls surviving and host weight gain approaching that seen with normal controls run in parallel observed. The therapy did not prevent death, but did increase mean survival times in a dose-responsive manner. $SaO_2$ levels remained high in these treated animals as well (Table 13, FIG. 5).

Figure 6:
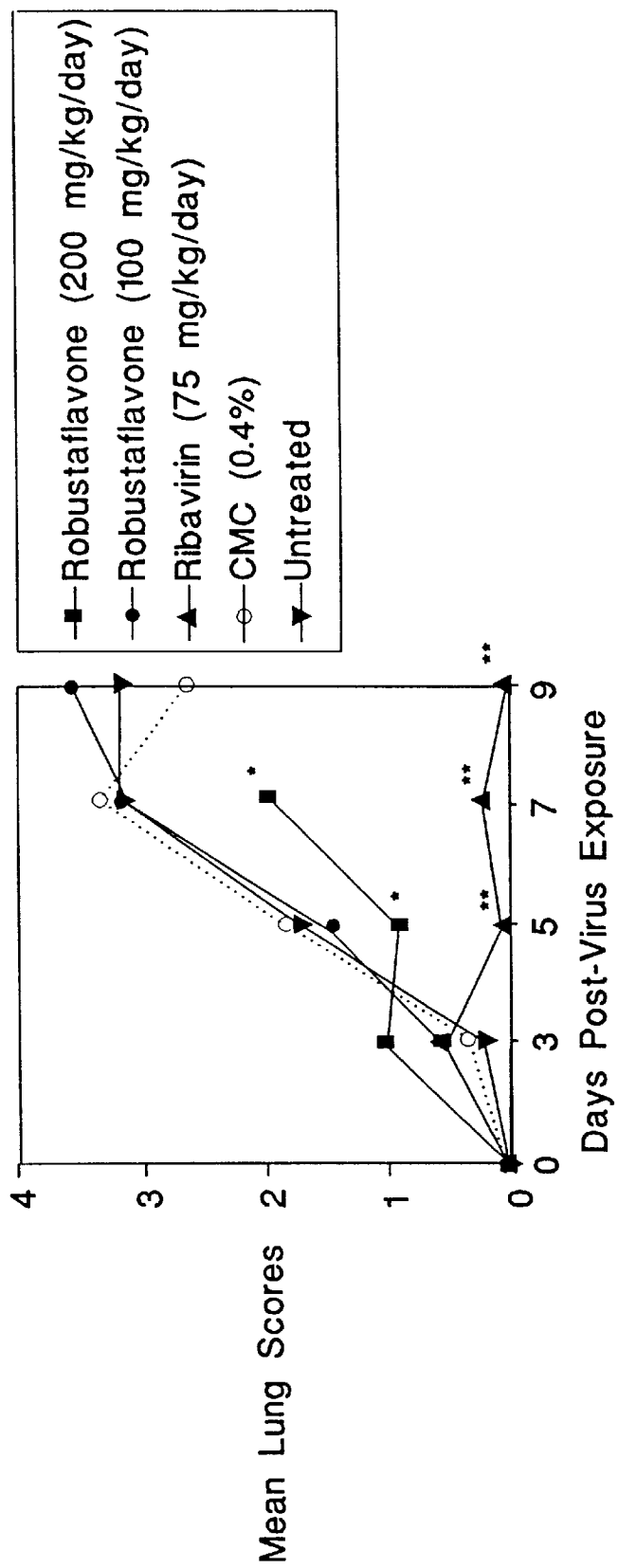
FIG. 6 illustrates the effect of treatment with robustaflavone in CMC on mean lung scores in Influenza A virus-infected mice as described in Example 10.
Figure 7:
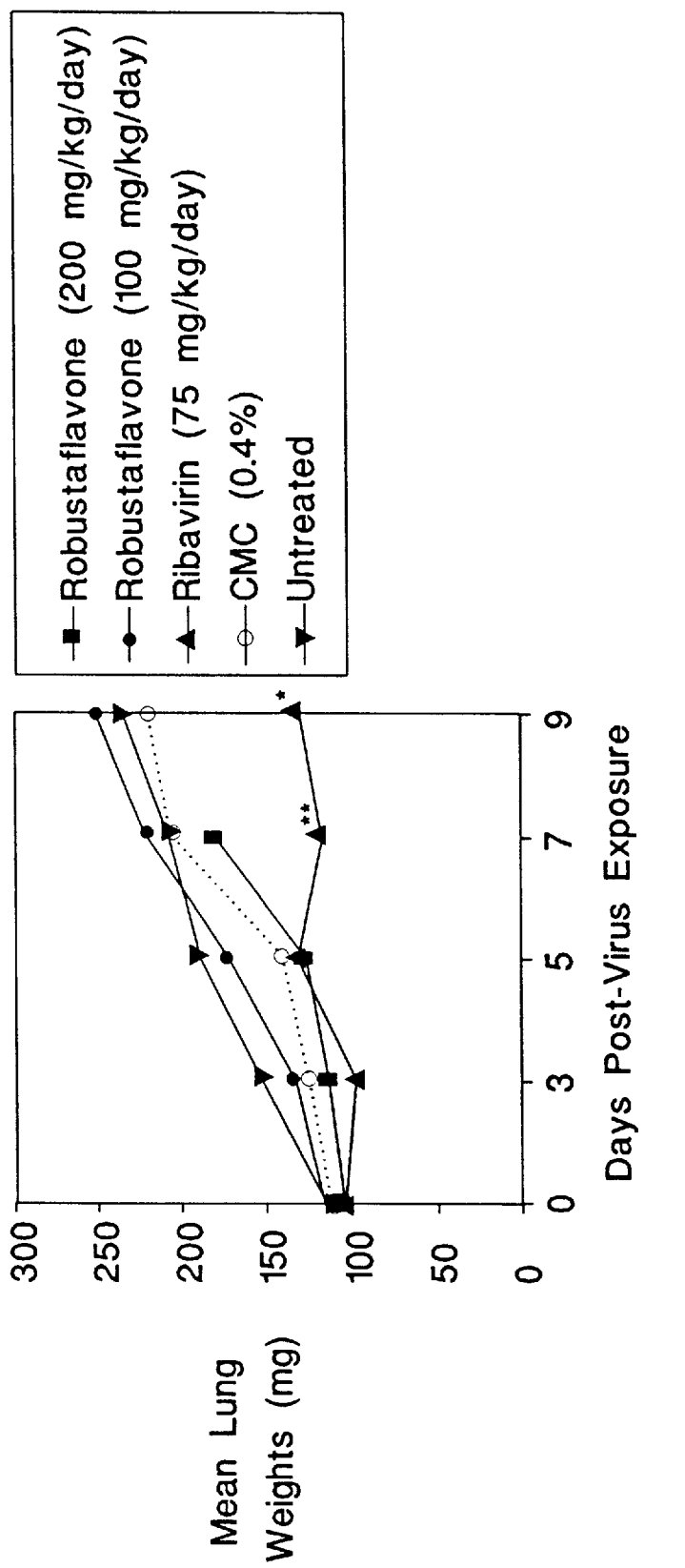
FIG. 7 illustrates the effect of treatment with robustaflavone in CMC on mean lung weights in Influenza A virus-infected mice as described in Example 10.
Figure 8:
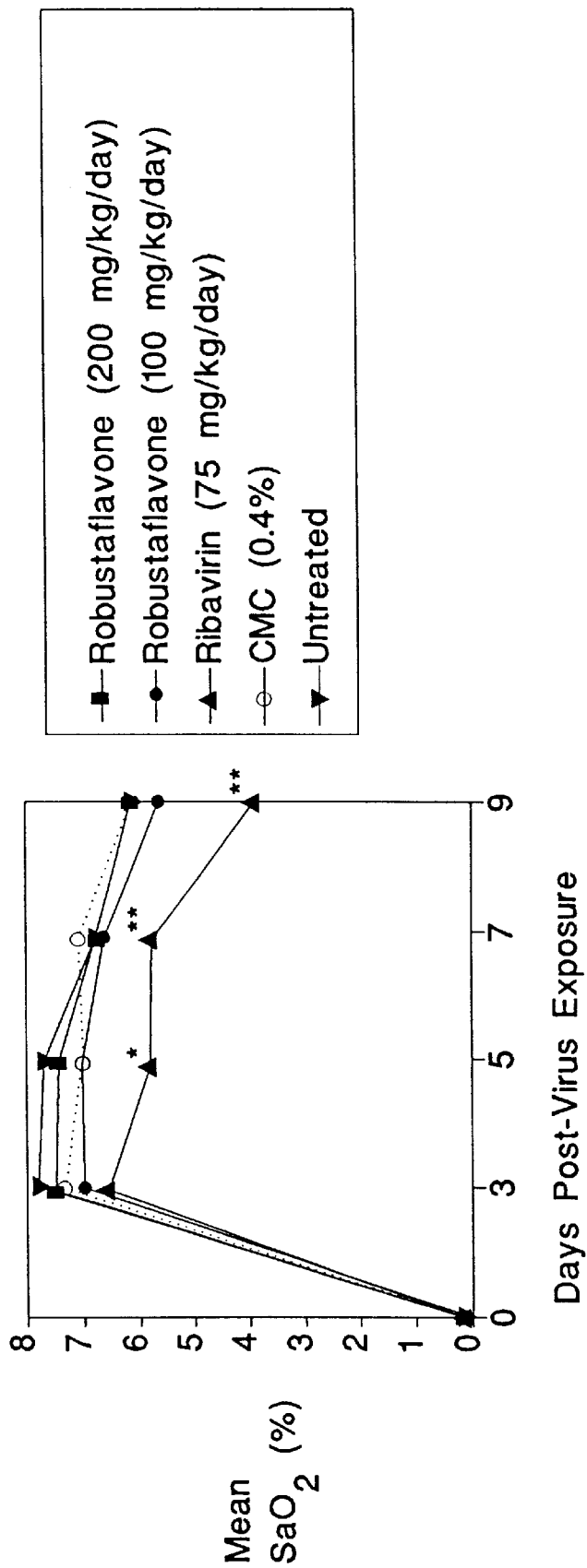
FIG. 8 illustrates the effect of treatment with robustaflavone in CMC on mean virus titers in Influenza A virus-infected mice as described in Example 10.

Treatment with this compound also inhibited lung consolidation in a dose-responsive fashion as seen in FIGS. 6 and 7.

These data indicate that: 1) Robustaflavone can be inhibitory to the in vivo influenza infection and 2) there is apparently at least a partial absorption of the compound since the dose-responsive effects were seen.

It may be pertinent to note that two flavones have previously been reported to have influenza virus-inhibitory effects. 5,7,8,4'-Tetrahydroxyflavone was reported in 1992[74] to prevent viral proliferation in lungs of infected mice when the compound was administered either by the intranasal or oral routes. The related 8-methylether compound, 5,7,4'-trihydroxy-8-methoxyflavone, was similarly effective when administered intranasally or by the i.p. routes.[74-77] Research by these investigators indicated the compounds reduce viral replication by inhibiting fusion of the virus with endosome/lysosome membrane which occurs at an early stage of the virus infection cycle and may also inhibit budding of the progeny virus from the cells surface.[77,78] The vehicle for these flavones was $Na_2CO_3$/saline.

Conclusion

The flavone robustaflavone was evaluated against influenza A/NWS/33 (H1N1) virus infections in mice using two vehicles, 0.4% carboxymethylcellulose (CMC) and 100% dimethylsulfoxide (DMSO). Treatment was i.p. twice daily for 5 days beginning 4 h pre-virus exposure. The compound in DMSO was toxic to the mice at the two dosages employed, 75 and 37.5 mg/kg/day; despite this toxicity, significant reduction in lung consolidation was seen. When used in CMC, the doses of 200 and 100 mg/kg/day used were well tolerated and both inhibited lung consolidation and slowed the mean day to death of the animals.

TABLE 11

Toxicological Effects of CMC, DMSO, DMSF, and PEG 200 in BALB/c Mice[1]

| Vehicle | Volume/ Injection (ml) | Surv/ Total | Mean Day To Death | Mean Host Wt. Change (g)[2] |
|---|---|---|---|---|
| 0.4% Carboxymethyl-cellulose (CMC) | 0.1 | 3/3 | >21 | 1.7 |
| 100% DMSO | 0.1 | 2/2 | >21 | -.26 |
| 100% DMSO | 0.05 | 1/2 | 4.0 | -0.3 |
| 100 DMF | 0.05 | 0/2 | 1.0 | 7 |
| 100% PEC 200 | 0.08 | 1/2 | 5.0 | -2.2 |
| 100% PEC 200 | 0.1 | 0/2 | 2.0 | -2.8 |

[1]Treatment i.p. bif × 5.
[2]Maximum difference between initial weight and weight after treatment.

TABLE 12

Effect of i.p. Treatment with Robustaflavone
in DMSO Vehicle on influenza A (H1N1) Virus
Infections in Mice
Animals: 13–15 g female BALB/c Mice
Virus: Influenza A (A/NWS/33 (H1N1), i.n.
Drug Diluent: Robustaflavone 0.4% DMSO; Ribavirin Saline
Treatment Schedule: bid × 5 beg −4 h pre-virus exposure
Treatment route: i.p.
Experiment Duration: 21 days

| | | Toxicity Controls | | | | |
|---|---|---|---|---|---|---|
| | Dosage | | Mean Weight | Infected, Treated | | |
| Compound | (mg/kg/ day) | Surv/ Total | Change (g)[a] | Surv/ Total | MST[b] (days) | Mean $SaO_2$[c] (%) |
| Robusta- | 75 | 0/3 | −1.7 | 0/9 | 3.2 | 70.6 |
| flavone | 37.5 | 1/3 | −0.8 | 0/10 | 8.0 | 73.8 |
| Ribavirin | 75 | 3/3 | −0.5 | 10/10** | >21.0** | 87.1** |
| DMSO | — | — | — | 0/20 | 9.6 | 82.6 |
| Untreated | — | — | — | 0/20 | 11.4 | 84.2 |
| Normals | — | 3/3 | 2.0 | — | — | 87.9 |

[a]Difference between initial weight at start of treatment and weight 18 h following final treatment of toxicity controls.
[b]Mean survival time of mice dying on or before day 21.
[c]Mean of days 3–10.
**P < 0.01 compared to DMSO-treated controls.

TABLE 13

Effect of i.p. Treatment with Robustaflavone
in CMC Vehicle on influenza A (H1N1) Virus
Infections in Mice
Animals: 13–15 g female BALB/c Mice
Virus: Influenza A (A/NWS/33 (H1N1), i.n.
Drug Diluent: Robustaflavone 0.4% CMC; Ribavirin Saline
Treatment Schedule: bid × 5 beg −4 h pre-virus exposure
Treatment route: i.p.
Experiment Duration: 21 days

| | | Toxicity Controls | | | | |
|---|---|---|---|---|---|---|
| | Dosage | | Mean Weight | Infected, Treated | | |
| Compound | (mg/kg/ day) | Surv/ Total | Change (g)[a] | Surv/ Total | MST[b] (days) | Mean $SaO_2$[c] (%) |
| Robusta- | 200 | 3/3 | 1.5 | 0/9 | 11.1 | 84.6** |
| flavone | 1005 | 4/4 | 1.9 | 0/10 | 9.8 | 85.1** |
| Ribavirin | 75 | 3/3 | −0.5 | 10/10** | >21.0** | 87.1** |
| CMC | — | — | — | 0/16 | 9.3 | 80.4 |
| Untreated | — | — | — | 0/20 | 11.4 | 84.2 |
| Normals | — | 3/3 | 2.0 | — | — | 87.9 |

[a]Difference between initial weight at start of treatment and weight 18 h following final treatment of toxicity controls.
[b]Mean survival time of mice dying on or before day 21.
[c]Mean of days 3–10.
**P < 0.01 compared to CMC-treated controls.

CONCLUSION

The results indicated that robustaflavone and robustaflavone tetrasulfate potassium salt were extremely effective anti-HBV agents. Robustaflavone also exhibited strong inhibitory effects against influenza A and influenza B viruses. Both hinokiflavone and robustaflavone demonstrated similar activity against HIV-1 RT, producing $IC_{50}$ values of 35.2 µg/mL and 33.7 µg/mL, respectively. Amentoflavone, agathisflavone, morelloflavone, GB-1a and GB-2a were moderately active against HIV-1 RT, with $IC_{50}$ values of 64.0 µg/mL, 53.8 µg/mL, 64.7 µg/mL, 127.8 µg/mL, and 94.6 µg/mL, respectively. Morelloflavone also demonstrated significant antiviral activity against HIV-1 (strain LAV in phytohemagglutinin (PHA)-stimulated human peripheral blood mononuclear (PBM) cells) at an EC50value of 5.7 µM and an SI value (selectivity index) of approximately 10. The other biflavanoids were either slightly active or inactive against these viruses and HIV-1 RT.

Amentoflavanone (1), agathisflavone (2) volkensiflavanone (5), volkensiflavone hexamethyl ether (6), rhusflavanone (9), and succedaneaflavone (11) exhibited inhibitory activity against influenza B virus with the selective index (SI) of 178, 5.6, 34, ~38, 9.3 and 15, respectively. Amentoflavone (1), and agathisflavone (2) also demonstrated anti-influenza A activity.

Robustaflavone (3) produced moderate inhibitory activity against both HSV-1 and HSV-2. Rhusflavanone (9) was active against HSV-2, while succedaneaflavanone hexaacetate (12) was moderately active against VZV.

References

1. Hoofnagle, J. H. Chronic hepatitis B, *N. Engl. J. Med.* 1990, 323, 337–339.

2. Aach, R. D. The treatment of chronic type B viral hepatitis. *Ann. Intern. Med.* 1988, 109, 88–91.

3. Martin, P. and Friedman, L. S. In *Innovations in Antiviral Development and the Detection of Virus Infections;* T. M. Block; D. Junkind; R. L. Crowell; M. Dension; L. R. Walsh, Ed.; Plenum Press: New York, 1992, 111–120.

4. Kaplan, M. M.; Webster, R. G. The epidemiology of influenza, *Sci. Am.,* 1977, 236 (6), 88–105.

5. Alexander, G. J.; Brahm, J.; Fagan, E. A.; Smith, H. M.; Daniels, H. M.; Eddleston, A. L.; Williams, R., Loss of HBSAg with interferon therapy in chronic hepatitis B virus infection. *Lancet* 1987, ii, 66–69.

6. Hoofnagle, J. H.; Di Bisceglie, A. M. Antiviral therapy of viral hepatitis. In *Antiviral Agents and Viral Diseases of Man;* G. J. Galasso; R. J. Whiteley; T. C. Merigan, Ed; Raven Press: New York, 1972, 415–457.

7. Yokosuka, O.; Omata, O. M.; Imazeki, F.; Okauda, K.; Summers, J. Changes of hepatitis B virus DNA in liver and serum caused by recombinant leukocyte interferon treatment: analysis of intrahepatic replicative hepatitis B virus DNA. *Hepatology* 1985, 5, 728–734.

8. Doong, S. L.; Tsai, C. H.; Schinazi, R. F.; Liota, D. C.; Cheng, Y. C. Inhibition of the replication of hepatitis B virus in vitro by 2',3'-dideoxy-3'-thiacytidine and related analogues. *Pro. Natl. Acad. Sci. USA* 1991, 88, 8495–99.

9. Schlam, S. W.; de Man, R. A.; Heijtink, R. A.; Niesters, G. M. New nucleoside analogues for chronic hepatitis B. *J. Hepatalogy* 1995, 22, 52–56.

10. van Leeuwen R.; Katlama, C.; Kitchen, V.; Boucher, C. A. B.; Tubiana, R.; McBride, M.; Ingrand, D.; Weber, J.; Hill, A.; McDade, H.; Danner, S. A. Evaluation of safety and efficacy of 3TC (Lamivudine) in patients with asymptomatic or mildly symptomatic human immunodeficiency virus infection: A phase I/II study. *J. Inf. Dis.* 1995, 171, 1166–71.

11. Hoffman, C. E. Amantadine HCl and related compounds. In *Selective Inhibitors of Viral Functions;* Carter, W. A., Ed.; CRC Press: Cleveland, 1973, 199.

12. Dolin, R.; Reichman, R. C.; Madore, H. P.; Maynard, R.; Lindon, P. M.; Webber-Jones, J. A controlled trial of amantadine and rimandatine in the prophylaxis of influenza A infections. *N. Engl. J. Med.* 1982, 307, 580–584.

13. Oxford, J. S.; Galbraith, A. Anti-influenza virus activity of amantadine: A selective review of laboratory and clinical data: In *Viral Chemotherapy;* Shugar D. Ed.; Pergamon Press, 1985, 169–254.

14. Couch, R. B.; Jackson, G. G. Antiviral agents in influenza—summary of influenza workshop VIII. *J. Infect. Dis.* 1976, 134, 516–527.

15. Bryson, Y. J.; Monahan, C.; Pollack, M.; Shields, W. D. A prospective double-blind study of side effects associated with the administration of amantadine for influenza A virus prophylaxis. *J. Infect. Dis.* 1980, 141, 543–547.

16. Tsunoda, A.; Maasab, H. H.; Cochran, K. W.; Eveland, W. C. Antiviral activity of α-methyl-1-adamantane methylamine hydrochloride. In *Antimicrob. Agents Chemother.* 1966, 553.

17. Tisdale, M.; Bauer, D. J. The relative potencies of anti-influenza compounds. *Ann. N. Y. Acad. Sci.* 1977, 284, 254–263.

18. Degelau, J; Somani, S. K.; Cooper, S. L.; Guay, D. R. P.; Crossley, K. B. Amantadine-resistant influenza A in a nursing facility. *Arch. Intern. Med.* 1992, 152, 390–392.

19. Hayden, F. G.; Belshe, R. B.; Clover, R. D.; Hay, A. J.; Oakers, M. G.; Soo, W. Emergence and apparent transmission of rimantadine-resistant influenza virus in families. *N. Engl. J. Med.* 1989, 321, 1696–1702.

20. Mast, E. E.; Harmon, M. W.; Gravenstein, S.; Wu, S. P.; Arden, H. H.; Circo, R.; Tyszka, G.; Kendal, A. P.; Davis, J. P. Emergence and possible transmission of amantadine-resistant viruses during nursing home outbreaks of influenza A (H3N2). *Am J. Epidemiol.* 1992, 134, 988–997.

21. Hayden, F. G.; Couch, R. B. Clinical and epidemiological importance of influenza A viruses resistant to amantadine and rimantadine. *Rev. Med. Virol.,* 1992, 2, 89–96.

22. Kimberlin, D. W.; Crampacker, C. S.; Straus, S. E.; Biron, K. K.; Drew, W. L.; Hayden, F. G.; McKinlay, M.; Richman, D. D.; Whitley, R. J. Antiviral resistance in clinical practice. *Antiviral Res.,* 1995, 26, 423–438.

23. Knight, V.; Gilbert, B. E. Ribavirin aerosol treatment of influenza. In *Infectious Disease Clinics of North America,* Vol 1.; Moellering, Jr.. Ed.; 1987, 441–57.

24. Ray, C. G.; Icenogle, T. B.; Minnich, L. L; Copeland, J. G.; Grogan, T. M. The use of intravenous ribavirin to treat influenza virus-associated acute myocarditis. *J. Infect Dis.,* 1989, 159, 829–836.

25. Lin, Y. M.; Chen, F. C. Robustaflavone from the seed-kernels of *Rhus succedanea. Phytochemistry,* 1974, 13, 1617–1619.

26. Mabry, T. J.; Markham, K. R.; Thomas, M. B. *The Systematic Identification of Flavonoids;* Springer, New York, 1970, 35–36.

27. Qasim, M. A.; Roy, S. K.; Ilyas, M. Phenolic Constituents of Selaginellaceae. *Indian Journal of Chemistry,* 1985, 24B, 220.

28. Arya, Ranjiana; Babu, Vikas; Ilyas, M.; Nasim, K. T. Phytochemical examination of the leaves of *Anaeardium occidentale. J. Indian Chem. Soc.,* 1989, 66, 67–68

29. Xu, L.; Chem, Z.; sun, N. *Zhiwu Xuebao,* 1993, 35, 138–143.

30. Lopez-Saez, J. A.; Perez-Alonso, M.; Negueruela, A. V. Biflavanoids of *Selaginella denticulata* growing in Spain. *Naturforsch.,* 1994, 49c, 267–270.

31. Silva, G. L.; Chai, H.; Gupta, M. P.; Farnsworth, N. R.; Cordell, G. A.; Pezzuto, J. M.; Beecher, C. W. W.; Kinghorn, A. D. Cytotoxic biflavanoids from *Selaginella willdenowii. Phytochemistry,* 1995, 40, 129–134.

32. Sidwell, R. W.; Bailey, D. W.; Wong, M. H.; Huffman, J. H.: In vitro and in vivo sensitivity of a non-mouse-adapted influenza (Beijing) virus infection to amantadine and ribavirin. *Chemotherapy,* 1995: 41, 455–461.

33. Anand, K. K.; Gupta, V. N.; Rangari, V.; Singh, B.; Chandan, B. K. Structure and hepatoprotective activity of a biflavonoid from *Ganarium manii. Planta Medica,* 1992, 58, 493–5.

34. Baba, K.; Takeuchi, K.; Mitsunobu, D.; Maisugi, K. The structures of new biflavonoids from *Daphne odora* Thunb. *Tennen Yuki Kagobutsu Toronkai Koen Yoshishu,* 1987, 29, 668–75 (Japan).

35. Bardos, T. J.; Schinazi, R. F. Ling, K.-H.; Heider, A. R. Structure-activity relationships and mode of action of 5-mercapto-substituted oligo- and polynucleotides as antitemplates inhibiting replication of human immunodeficiency virus type 1. *Antimicrob. Agents Chemother.,* 1992, 36, 108–114.

36. Barre-Sinoussi, F.; Chermann, J. C.; Rey, R.; Nugeyre, L. M. T.; Chamaret, S.; Gruest, J.; Dauguet, C.; Axler-Blin, C.; Vezinet-Brun, F.; Rouzioux, C.; Rozenbaum, W., and Montagnier, L. Isolation of a T-lymphotopic retrovirus from a patient at risk for acquired immune deficiency syndrome (AIDS). *Science,* 1983, 220, 868–871.

37. Chen, F. C.; Lin, Y. M. Rhusflavanone, a new biflavanone from the seeds of wax tree. *J. Chem. Soc., Perkin Trans.,* 1976, I, 98–101.

38. Chen, F. C.; Lin, Y. M. Succedaneaflavanone—A new 6, 6"-biflavanone from *Rhus succedanea. Phytochemistry,* 1975A, 14, 1644–1647.

39. Chen, F. C.; Lin, Y. M.; Hung, J. G. Phenolic compounds from the heartwood of *Gracinia multiflora. Phytochemistry,* 1975B, 14, 300–303.

40. Chen, F. C.; Lin, Y. M.; Hung, J. C. A new biflavanone glucoside from *Garcinia multiflora. Phytochemistry,* 1975C, 14, 818–820.

41. Cholla, M. R.; Paya, M.; Alcaraz, M. J. Inhibitory effects of phenolic compounds on $CCl_4$ induced microsomal lipid peroxidation. *Experientia,* 1991, 47, 195–199.

42. Chou, T.-C.; Talalay, P. Quantitative analysis of dose-effect relationships: The combined effects of multiple drugs or enzyme inhibitors. *Adv. Enz. Regul.,* 1984, 22, 27–35.

43. Chou, J.; Chou, T.-C. Dose-effect analysis with microcomputers: Quantitation of $ED_{50}$, $LD_{50}$, synergism, antagonism, low-dose risk, receptor binding and enzyme kinetics. A computer software for Apple II series and IBM-PC and Instruction Manual. 1985, Elsevier Science Publishers, Cambridge, U.K.

44. Furukawa, S. (1932) *Sci. Papers Inst. Phy. Chem.,* 1932, 19, 27, (Japan).

45. Furukawa, S. (1933) *Sci. Papers Inst. Phy. Chem.,* 1933, 21, 273–278, (Japan).

46. Gallo, R. C.; Salahuddin, S. Z.; Popovic, M.; Shearer, G. M.; Kaplan, M.; Haynes, B. F.; Palker, T. J.; Redfield, R.; Oleske, J.; Safai, B.; White, G.; Foster, P.; Markham, P. D. Frequent and detection and isolation of cytopathic retroviruses (HTLV-III) from patients with AIDS and at risk for AIDS. *Science,* 1984, 224, 500–503

47. Tan, G. T.; Pezzuto J. M.; Kinghorn, A. D. Evaluation of natural products as inhibitors of human immunodeficienct virus Type 1 (HIV-1) reverse transcriptase. *J. Nat. Prod.,* 1991, 54, 143.

48. Hayashi, T.; Morita, N. Mechanism of action of the antiherpesvirus biflavone ginkgetin. *Antimicrob. Agents Chemother.,* 1992, 36, 1890–3.

49. Iwu, M. M.; Igbokao, O. A.; Onwuchekwa, U. A; Okunii, C. O. Evaluation of the antihepatotoxic activity of the biflavonoids of Garcinia kola seed. J. Ethnopharmacol., 1987, 21, 127–38.

50. Iwu, M. M.; Igbokao, D. A.; Okunji, D. D.; Tempesta, M. Antidiabetic and aldose reductase activities of biflavanones of Gracinia kola. J. Pharm. Pharmacol., 1990, 42, 290–2.

51. Konoshima, T.; Takasaki, M.; Kozuka, M.; Lin, Y. M.; Chen, F. C.; Tokuda, H.; Matsumoto, T. Studies on inhibitors of skin tumors promotion (IV). Inhibitory effects of flavonoids on Epstein-Barr virus activation (1). Shoyakugaku Zasshi, 1988, 42, 343–6.

52. Kozuka, M.; Tokuda, H.; Matsumoto, T. Hinokiflavone and kayaflavone as antiviral agents. Jpn. Kokai Tokkyo Koho JP 01,221,314 [89,221,314] (Cl. A61K31/35), 04 September 1989, Appl. 88/44,251, Feb. 29, 1988.

53. Lin, Y. M.; Chen, F. C.; Liang, C. M. Biflavonyls from drupes of Rhus succedanea. Phytochemistry, 1974A, 12, 276–7.

54. Lin, Y. M.; Chen, F. C. Agathisflavone from the drupes of Rhus succedanea. Phytochemistry, 1974B, 13, 657–658.

55. Lin, Y. M.; Chen, F. C. Robustaflavone from the seed kernels of Rhus succedanea. Phytochemistry, 1974C, 13, 1617–1619.

56. Lin, Y. M.; Chen, F. C.; Lee, K. H. Hinokiflavone, a cytotoxic principle from Rhus succedanea and the cytotoxicity of the related biflavonoids. Planta Medica, 1989, 55, 166–8.

57. MAPE establishment (1987) Ger. Offen. DE 3,544, 457 (Cl. C07D311/40), Jun. 19, 1987, Appl. Dec. 16. 1985).

58. McDougal, J. S.; Cort, S. P.; Kennedy, M. S.; Cabridilla, C. D.; Feorino, P. M.; Francis, D. P.; Hicks, K.; Kalyanaramen, V. S.; Martin, L. S. Immunoassay for the detection and quantitation of infectious human retrovirus, lymphadenopathy-associated virus (LAV). J. Immun. Meth. 1985, 76, 171–183.

59. Mora, A.; Paya, M.; Roips, K. Structure-activity relationships of polymethoxyflavones and other flavonoids as inhibitor of non-enzymatic lipid peroxidation. Biochem-Pharmacol., 1990, 40, 793–7.

60. Murakami, A.; Ohigashi, H.; Jisaka, M.; Irie, R.; Koshimizu, K. Cancer Lett. (Shannon, Irel.), 1991, 58, 101–6.

61. Nakazawa, K. The Chemical Structure of Ginkgetin. Gifu Yakka Diagaku. Kiyo, 1941, 12, 1, Chem. Abst. 59,2759d.

62. Natarajan, S.; Murti, V. V. S.; Seshadri, T. R.; Ramaswamy, A. S. Some new pharmacological properties of flavonoids and biflavonoids. Current Science, 1970, 39, 553.

63. Ono, K.; Nakane, H.; Jukushima, M.; Chgermann, J. K.; Barre-Sinlussi, F. Inhibition of reverse transcriptase activity by a flavonoid compound, 5,6,7-trihydroxyflavone. Biochem. Biophys. Res. Commu., 1989, 160, 982–7.

64. Ono, K.; Nakane, H.; Jukushima, M.; Chgermann, J. K.; Barre-Sinlussi, F. Differential inhibitory effects of various flavonoids on the activities of reverse transcriptase and cellular DNA and RNA polymerases. Euro. J. Biochem., 1990, 190, 469–476.

65. Okunji, C. O.; Iwu, M. M. Molluscicidal activity of Garcinia kola biflavanone. Fitoterapia, 1991, 62, 74–6.

66. Sanz, M. J.; Ferrandiz, M. J.; Cejudo, M.; Terencia, M. C.; Gil, B.; Bustos, G.; Ubeda, A.; Gunasegaran, R.; Alcaraz, M. M. Influence of a series of natural flavonoids on free radical generating systems and oxidative stress. J. Xenobiotica, 1994, 24, 689–99.

67. Schinazi, R. F.; Cannon, D. L.; Arnold, B. H.; Martino-Saltzman, D. Combination of isoprinosine and 3'-azido-3'-deoxythymidine in lymphocytes infected with human immunodeficiency virus type 1. Antimicrob. Agents Chemother., 1988, 32, 1784–1787.

68. Schinazi, R. F.; Sommadossi, J. P.; Saalmann, V.; Cannan, M. W.; Hart, G.; Smith, G.; Hahn, E. Activity of 3'-azido-3'-deoxythimidine nucleotide dimmers in primary lymphocytes infected with human immunideficiency virus type 1. Antimicrob. Agents Chemother., 1990, 34, 1061–1067.

69. Spira, T. J.; Bozeman, L. H.; Holman, R. C.; Warfield, K. T.; Phillips, S. K.; Feoprino, P. M. Micromethod for assaying the reverse transcriptase of LAV-HTIV-III/lymphadenopathy-associated virus. J. Clin. Microbiol., 1987, 25, 97–99.

70. Tan, G. T.; Pezzuto, J. M.; Kinghorn, A. D. Evaluation of natural products as inhibitors of human immunodeficiency virus type 1 (HIV-1) reverse transcriptase. J. Nat. Prod., 1991, 54, 143–154.

71. Tokuda, F.; Matsumoto, T. Bilobetin as virus genome inactivating agent JPN. Kokai Tokkyo Koho JP 01 42,426 [89 42,426] (Cl. A61k31/35), Feb 14, 1989, Appl. 87/200, 570, Aug. 11, 1987.

72. Sidwell, R.; Huffman, R.; Gilbert. B.; Moscon, G.; Pedersen, R.; Burger, R.,; Warren, R. Utilization of pulse oximetry for the study of the inhibitory effects of antiviral agents on influenza virus in mice. Antimicrob. Ag. Chemother., 1992, 36, 473–476.

73. Sidwell, R. W.; Huffman, J. H.; Call, E. W., Alaghamandan, H.; Cook, P. D.; Muce, R. K. Antiviral Res., 1995, 6, 343–353.

74. Nagai, T.; Miyaichi, Y.; Tomimori, T.; Suzuki, Y.; Yamada, N. Inhibition of influenza virus sialidase and anti-influenza virus activity by plant flavonoids. Chem. Pharm. Bull., 1990, 38, 1329–32.

75. Nagai, T.; Miyaichi, Y.; Tomimore, T.; Suzuki, Y.; Yamada, H. In vivo anti-influenza virus activity of plant flavonoids possessing inhibitory activity for influenza virus sialidase. Antiviral Res., 1990, 19:207–17.

76. Nagai, T.; Suzuki, Y.; Tomimore, T.; Yamada, H. Antiviral activity of plant flavonoid, 5,7,4'-trihydroxy-8-methoxyf lavone, from roots of Scutellaria baicalenais against influenza A (H3N2) and B viruses. Biol. Pharm. Bull., 1995, 18, 295–9.

77. Nagai, T.; Moriguchi, R.; Suzuki, Y.; Tomimori, T.; Yamada, H. Mode of action of the anti-influenza virus activity of plant flavonoid, 5,7,4'-trihydroxy-8-methoxyflavone, form the roots of Scutellaria baicalensis. Antiviral Res., 1995, 26, 11–25.

78. Huang, L.; Kashiwade, Y.; Cosentino, L. M.; Fan, S.; Chen, C. H.; McPhail, A. T.; Fujoika, T.; Mihasha, K.; and Lee, K. H. Anti-AIDS Agents. 15. Synthesis and Anti-HIV Activity of Dihydroseselins and Related Analogs. J. Med. Chem., 1994, 37, 3947–3955.

79. Magri, N. J.; Kinston, D. G. I. Modified Toxols, 4. Synthesis and Biological Activity of Toxols Modified in the Side Chain. J. Nat. Prod., 1987, 51, 298–306.

80. Barron, D.; Ibrahim, R. K. Synthesis of flavanoid sulfates: 1. stepwise sulfation of position, 3,7, and 4' using N,N'-dicyclohexycarbodiimide and tetrabutylamminium hydrogen sulfate. Tetrahedron, 1987, 43, 5197–5202.

81. Korba, B. E.; Milman, G. A cell culture assay for compounds which inhibit hepatitis B virus replication. Antiviral Res., 1991, 15, 217–218.

82. Korba, B. E.; Gerin, J. L. Use of a standardized cell culture assay to assess activities of nucleoside analogs against hepatitis B virus replication. *Antiviral Res.,* 1992, 19, 55–70.

83. Muller, C.; Bergmann, K. F.; Gerin, J. L.; Korba, B. E. Production of hepatitis B virus by stably transfected monocytic cell line U-937: a model for extrahepatic hepatitis B virus replication. *J. Infect. Dis.,* 1992, 165, 929–933.

What we claim:

1. A method for isolating substantially purified robustaflavone from the plant *Rhus succedanea,* which method comprises isolating and extracting robustaflavone from a crude yellow pigment extract derived from plant material of *Rhus succedanea* with a solvent mixture of toluene/ethanol/formic acid.

2. The method according to claim 1, further comprising the steps of:

(a) providing a crude yellow pigment extract from *Rhus succedanea;*

(b) adsorbing the extract onto silica gel;

(c) washing the silica gel with a solvent mixture of toluene/ethanol/formic acid and drying the silica gel;

(d) eluting the silica gel with a first solvent mixture of toluene/ethanol/formic acid to remove non-robustaflavone biflavanoids; and (e) eluting the silica gel with a second solvent mixture of ethanol/pyridine to obtain substantially pure robustaflavone.

3. The method according to claim 2, wherein said toluene/ethanol/formic acid is at a volume ratio of about 10–30:2–10:1.

4. The method according to claim 3, wherein said toluene/ethanol/formic acid is at a volume ratio of about 20:5:1.

5. The method according to claim 2, wherein said ethanol/pyridine is at a volume ratio of about 3–5:1.

6. The method according to claim 5, wherein said ethanol/pyridine is at a volume ratio of about 4:1.

7. The method according to claim 2, wherein said plant material consists of seeds, leaves, stems, twigs, fruits, flowers, wood, bark or roots of *Rhus succedanea.*

8. The method according to claim 7, wherein said plant material is seed kernals of *Rhus succedanea.*

* * * * *